(12) United States Patent
Otsuna et al.

(10) Patent No.: US 8,183,017 B2
(45) Date of Patent: *May 22, 2012

(54) METHOD OF PRODUCING L-LYSINE

(75) Inventors: Seiko Otsuna, Kawasaki (JP);
Masakazu Sugimoto, Kawasaki (JP);
Masako Izui, Kawasaki (JP); Atsushi Hayakawa, Kawasaki (JP); Eiichi Nakano, Kawasaki (JP); Masaki Kobayashi, Kawasaki (JP); Yasuhiko Yoshihara, Kawasaki (JP); Tsuyoshi Nakamatsu, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/915,793

(22) Filed: Oct. 29, 2010

(65) Prior Publication Data

US 2011/0065153 A1 Mar. 17, 2011

Related U.S. Application Data

(60) Continuation of application No. 10/226,136, filed on Aug. 23, 2002, now Pat. No. 7,846,698, which is a division of application No. 08/952,967, filed as application No. PCT/JP96/01511 on Jun. 5, 1996, now abandoned.

(30) Foreign Application Priority Data

Jun. 7, 1995 (JP) .................................. 1995-140614

(51) Int. Cl.
*C12P 13/04* (2006.01)
*C12P 21/04* (2006.01)

(52) U.S. Cl. ..................... 435/106; 435/252.3; 435/115; 435/172.5

(58) Field of Classification Search .................. None
See application file for complete search history.

(56) References Cited

U.S. PATENT DOCUMENTS

| | | | |
|---|---|---|---|
| 5,688,671 | A | 11/1997 | Sugimoto et al. |
| 5,804,414 | A | 9/1998 | Moriya et al. |
| 6,004,773 | A | 12/1999 | Araki et al. |
| 6,893,852 | B1 | 5/2005 | Izui et al. |
| 6,905,819 | B1 | 6/2005 | Matsuzaki et al. |
| 7,244,569 | B2 | 7/2007 | Matsuzaki et al. |
| 7,351,571 | B2 | 4/2008 | Nakamatsu et al. |
| 7,608,437 | B2 | 10/2009 | Asakura et al. |
| 2003/0054506 | A1 | 3/2003 | Otsuna et al. |
| 2004/0121428 | A1 | 6/2004 | Sugimoto et al. |
| 2008/0241895 | A1 | 10/2008 | Suzuki et al. |
| 2009/0258398 | A1 | 10/2009 | Nakamatsu et al. |

FOREIGN PATENT DOCUMENTS

| | | |
|---|---|---|
| EP | 0 435 132 | 7/1991 |
| EP | 0 699 759 | 3/1996 |
| EP | 0 733 710 | 9/1996 |
| EP | 0 811 682 | 12/1997 |
| EP | 9 811 682 | 12/1997 |
| EP | 1 172 437 | 1/2002 |
| JP | 7-7557 | 3/1995 |
| JP | 7-75578 | 3/1995 |
| WO | 94/25605 | 11/1994 |

OTHER PUBLICATIONS

Bonnassie, S., et al., "Nucleotide sequence of the *dapA* gene from *Corynebacterium glutamicum*," Nucleic Acids Res. 1990;18(21):6421.
Canadian Office Action for Canadian Appl. No. 2,224,058, dated Sep. 7, 2005.
Communication Pursuant to Rule 114(2) EPC fro EP Patent App. No. 96916305.4 (Oct. 30, 2009).
Office Communication from the European Patent Office for EP Patent App. 96916305.4 (Mar. 25, 2008) with English translation.
Supplementary Search Report for EP Appl. No. EP 96 91 6305 (May 30, 2005).
Creamer, J., et al., "Regulation of Enzymes of Lysine Biosynthesis in *Corynebacterium glutamicum*," J. Gen. Microbiol. 1988;134:3221-3229.
Eikmanns, B. J., et al., "Molecular aspects of lysine, threonine, and isoleucine biosynthesis in *Corynebacterium glutamicum*," Antonie van Leeuwenhoek 1993;64:145-163.
Graves, L. M., et al., "Aspartokinase III, a New Isozyme in *Bacillus subtilis* 168," J. Bacteriol. 1990;172(1):218-223.
Hänel, F., et al., "Control of the Aspartokinase of *Streptomyces noursei* and Its AEC-Resistant Mutants," Biotechnol. Lett. 1985;7(8):557-562.
Hernándo-Rico, V., et al., "Structure of the *ask-asd* operon and formation of aspartokinase subunits in the cephamycin producer '*Amycolatopsis lactamdurans*'," Microbiol. 2001;147:1547-1555.
Jetten, M. S. M., et al., "Recent Advances in the Physiology and Genetics of Amino Acid-Producing Bacteria," Critical Rev. Biotechnol. 1995;15(1):73-103.
Kalinowski, J., et al., "Genetic and biochemical analysis of the aspartokinase from *Corynebacterium glutamicum*," Mol. Microbiol. 1991;5:1197-1204.
Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.

(Continued)

*Primary Examiner* — Richard Hutson
(74) *Attorney, Agent, or Firm* — Shelly Guest Cermak; Cermak Nakajima LLP

(57) ABSTRACT

The ability and speed with which a coryneform bacterium can produce L-lysine are improved when the coryneform bacterium contains an aspartokinase in which feedback inhibition by L-lysine and L-threonine is substantially desensitized. This is accomplished by successively enhancing the DNA coding for dihydrodipicolinate reductase, the DNA coding for dihydrodipicolinate synthase, the DNA coding for diaminopimelate decarboxylase, and the DNA coding for diaminopimelate dehydrogenase.

12 Claims, 14 Drawing Sheets

OTHER PUBLICATIONS

Pisabarro, A., et al., "A Cluster of Three Genes (*dapA, orf 2*, and *dapB*) of *Brevibacterium lactofermentum* Encodes Dihydrodipicolinate Synthase, Dihydrodipicolinate Reductase, and a Third Polypeptide of Unknown Function," J. Bacteriol. 1993;175(9):2743-2749.

Applied and Environmental Microbiology, vol. 57, No. 6 (1991), Hermann Salim, et al., see pp. 1746-1752.

Nucleic Acids Res., vol. 15, No. 9 (1987), Kazumi Araki, et al., see. p. 3917.

Molecular Microbiology, vol. 4, No. 11, (1990), A. J. Sinskey, et al., see pp. 1819-1830.

Molecular and General Genetics, vol. 212, No. 1, (1988), A. J. Sinskey, et al., see pp. 112-119.

Rudinger (1976) Characteristics of the amino acids as components of a peptide hormone sequence. In: Peptide Hormones. Ed. J.A. Parsons. University Park Press, Baltimore, MD, pp. 1-7.

Ngo et al. (1994) Computational complexity, protein structure prediction, and the llevinthal paradox. In: The Protein Folding Problem and Tertiary Structure Prediction. Eds. Merz et al. Birkhauser et al., Boston, MA, pp. 491-495.

Thornton et al. (1995) Protein Engineering: Editorial Overview. Current Opinion in Biotechnology 6(4): 367-369.

Wallace (1993) Understanding cytochrome c function: engineering protein structure by semisynthesis. The FASEB Journal 7: 505-515.

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: NO (xi) SEQUENCE DESCRIPTION: SEQ ID NO: 1:

TCGCGAAGTA GCACCTGTCA CTT        23

(2) INFORMATION FOR SEQ ID NO: 2:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: other..synthetic DNA
    (A) DESCRIPTION: /desc = "synthetic DNA"

(iv) ANTI-SENSE: YES (xi) SEQUENCE DESCRIPTION: SEQ ID NO: 2:

ACGGAATTCA ATCTTACGGC C                                              21

(2) INFORMATION FOR SEQ ID NO: 3:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
        (A) ORGANISM: Brevibacterium lactofermentum
        (B) STRAIN: ATCC 13869

(xi) SEQUENCE DESCRIPTION: SEQ ID NO: 3:

TCGCGAAGTA GCACCTGTCA CTTTTGTCTC AAATATTAAA TCGAATATCA ATATACGGTC      60

TGTTTATTGG AACGCATCCC AGTGGCTGAG ACGCATCCGC TAAAGCCCCA GGAACCCTGT     120

GCAGAAAGAA AACACTCCTC TGGCTAGGTA GACACAGTTT ATAAAGGTAG AGTTGAGCGG     180

GTAACTGTCA GCACGTAGAT CGAAAGGTGC ACAAAGGTGG CCCTGGTCGT ACAGAAATAT     240

GGCGGTTCCT CGCTTGAGAG TGCGGAACGC ATTAGAAACG TCGCTGAACG GATCGTTGCC     300

ACCAAGAAGG CTGGAAATGA TGTCGTGGTT GTCTGCTCCG CAATGGGAGA CACCACGGAT     360

GAACTTCTAG AACTTGCAGC GGCAGTGAAT CCCGTTCCGC CAGCTCGTGA AATGGATATG     420

CTCCTGACTG CTGGTGAGCG TATTTCTAAC GCTCTCGTCG CCATGGCTAT TGAGTCCCTT     480

GGCGCAGAAG CTCAATCTTT CACTGGCTCT CAGGCTGGTG TGCTCACCAC CGAGCGCCAC     540

GGAAACGCAC GCATTGTTGA CGTCACACCG GGTCGTGTGC GTGAAGCACT CGATGAGGGC     600

AAGATCTGCA TTGTTGCTGG TTTTCAGGGT GTTAATAAAG AAACCCGCGA TGTCACCACG     660

TTGGGTCGTG GTGGTTCTGA CACCACTGCA GTTGCGTTGG CAGCTGCTTT GAACGCTGAT     720

GTGTGTGAGA TTTACTCGGA CGTTGACGGT GTGTATACCG CTGACCCGCG CATCGTTCCT     780

AATGCACAGA AGCTGGAAAA GCTCAGCTTC GAAGAAATGC TGGAACTTGC TGCTGTTGGC     840

TCCAAGATTT TGGTGCTGCG CAGTGTTGAA TACGCTCGTG CATTCAATGT GCCACTTCGC     900

GTACGCTCGT CTTATAGTAA TGATCCCGGC ACTTTGATTG CCGGCTCTAT GGAGGATATT     960

CCTGTGGAAG AAGCAGTCCT TACCGGTGTC GCAACCGACA AGTCCGAAGC CAAAGTAACC    1020

GTTCTGGGTA TTTCCGATAA GCCAGGCGAG GCTGCCAAGG TTTTCCGTGC GTTGGCTGAT    1080

GCAGAAATCA ACATTGACAT GGTTCTGCAG AACGTCTCCT CTGTGGAAGA CGGCACCACC    1140

GACATCACGT TCACCTGCCC TCGCGCTGAC GGACGCCGTG CGATGGAGAT CTTGAAGAAG    1200

CTTCAGGTTC AGGGCAACTG GACCAATGTG CTTTACGACG ACCAGGTCGG CAAAGTCTCC    1260

CTCGTGGGTG CTGGCATGAA GTCTCACCCA GGTGTTACCG CAGAGTTCAT GGAAGCTCTG    1320

CGCGATGTCA ACGTGAACAT CGAATTGATT TCCACCTCTG AGATCCGCAT TTCCGTGCTG    1380

ATCCGTGAAG ATGATCTGGA TGCTGCTGCA CGTGCATTGC ATGAGCAGTT CCAGCTGGGC    1440

GGCGAAGACG AAGCCGTCGT TTATGCAGGC ACCGACGCGT AAAGTTTTAA AGGAGTAGTT    1500

TTACAATGAC CACCATCGCA GTTGTTGGTG CAACCGGCCA GGTCGGCCAG GTTATGCGCA    1560

```
CCCTTTTGGA AGAGCGCAAT TTCCCAGCTG ACACTGTTCG TTTCTTTGCT TCCCCGCGTT     1620

CCGCAGGCCG TAAGATTGAA TTC                                             1643

(2) INFORMATION FOR SEQ ID NO: 4:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 217..1482

(xi) SEQUENCE DESCRIPTION: SEQ ID NO: 4:

TCGCGAAGTA GCACCTGTCA CTTTTGTCTC AAATATTAAA TCGAATATCA ATATACGGTC       60

TGTTTATTGG AACGCATCCC AGTGGCTGAG ACGCATCCGC TAAAGCCCCA GGAACCCTGT      120

GCAGAAAGAA AACACTCCTC TGGCTAGGTA GACACAGTTT ATAAGGTAG AGTTGAGCGG      180

GTAACTGTCA GCACGTAGAT CGAAAGGTGC ACAAAG GTG GCC CTG GTC GTA CAG       234
                                       Met Ala Leu Val Val Gln
                                         1               5

AAA TAT GGC GGT TCC TCG CTT GAG AGT GCG GAA CGC ATT AGA AAC GTC       282
Lys Tyr Gly Gly Ser Ser Leu Glu Ser Ala Glu Arg Ile Arg Asn Val
         10                  15                  20

GCT GAA CGG ATC GTT GCC ACC AAG AAG GCT GGA AAT GAT GTC GTG GTT       330
Ala Glu Arg Ile Val Ala Thr Lys Lys Ala Gly Asn Asp Val Val Val
             25                  30                  35

GTC TGC TCC GCA ATG GGA GAC ACC ACG GAT GAA CTT CTA GAA CTT GCA       378
Val Cys Ser Ala Met Gly Asp Thr Thr Asp Glu Leu Leu Glu Leu Ala
     40                  45                  50

GCG GCA GTG AAT CCC GTT CCG CCA GCT CGT GAA ATG GAT ATG CTC CTG       426
Ala Ala Val Asn Pro Val Pro Pro Ala Arg Glu Met Asp Met Leu Leu
 55                  60                  65                  70

ACT GCT GGT GAG CGT ATT TCT AAC GCT CTC GTC GCC ATG GCT ATT GAG       474
Thr Ala Gly Glu Arg Ile Ser Asn Ala Leu Val Ala Met Ala Ile Glu
                 75                  80                  85

TCC CTT GGC GCA GAA GCT CAA TCT TTC ACT GGC TCT CAG GCT GGT GTG       522
Ser Leu Gly Ala Glu Ala Gln Ser Phe Thr Gly Ser Gln Ala Gly Val
             90                  95                 100

CTC ACC ACC GAG CGC CAC GGA AAC GCA CGC ATT GTT GAC GTC ACA CCG       570
Leu Thr Thr Glu Arg His Gly Asn Ala Arg Ile Val Asp Val Thr Pro
        105                 110                 115

GGT CGT GTG CGT GAA GCA CTC GAT GAG GGC AAG ATC TGC ATT GTT GCT       618
Gly Arg Val Arg Glu Ala Leu Asp Glu Gly Lys Ile Cys Ile Val Ala
    120                 125                 130

GGT TTT CAG GGT GTT AAT AAA GAA ACC CGC GAT GTC ACC ACG TTG GGT       666
Gly Phe Gln Gly Val Asn Lys Glu Thr Arg Asp Val Thr Thr Leu Gly
135                 140                 145                 150

CGT GGT GGT TCT GAC ACC ACT GCA GTT GCG TTG GCA GCT GCT TTG AAC       714
Arg Gly Gly Ser Asp Thr Thr Ala Val Ala Leu Ala Ala Ala Leu Asn
                155                 160                 165

GCT GAT GTG TGT GAG ATT TAC TCG GAC GTT GAC GGT GTG TAT ACC GCT       762
Ala Asp Val Cys Glu Ile Tyr Ser Asp Val Asp Gly Val Tyr Thr Ala
```

```
                    170                 175                 180
GAC CCG CGC ATC GTT CCT AAT GCA CAG AAG CTG GAA AAG CTC AGC TTC       810
Asp Pro Arg Ile Val Pro Asn Ala Gln Lys Leu Glu Lys Leu Ser Phe
            185                 190                 195

GAA GAA ATG CTG GAA CTT GCT GCT GTT GGC TCC AAG ATT TTG GTG CTG       858
Glu Glu Met Leu Glu Leu Ala Ala Val Gly Ser Lys Ile Leu Val Leu
200                 205                 210

CGC AGT GTT GAA TAC GCT CGT GCA TTC AAT GTG CCA CTT CGC GTA CGC       906
Arg Ser Val Glu Tyr Ala Arg Ala Phe Asn Val Pro Leu Arg Val Arg
215                 220                 225                 230

TCG TCT TAT AGT AAT GAT CCC GGC ACT TTG ATT GCC GGC TCT ATG GAG       954
Ser Ser Tyr Ser Asn Asp Pro Gly Thr Leu Ile Ala Gly Ser Met Glu
            235                 240                 245

GAT ATT CCT GTG GAA GAA GCA GTC CTT ACC GGT GTC GCA ACC GAC AAG      1002
Asp Ile Pro Val Glu Glu Ala Val Leu Thr Gly Val Ala Thr Asp Lys
            250                 255                 260

TCC GAA GCC AAA GTA ACC GTT CTG GGT ATT TCC GAT AAG CCA GGC GAG      1050
Ser Glu Ala Lys Val Thr Val Leu Gly Ile Ser Asp Lys Pro Gly Glu
            265                 270                 275

GCT GCC AAG GTT TTC CGT GCG TTG GCT GAT GCA GAA ATC AAC ATT GAC      1098
Ala Ala Lys Val Phe Arg Ala Leu Ala Asp Ala Glu Ile Asn Ile Asp
280                 285                 290

ATG GTT CTG CAG AAC GTC TCC TCT GTG GAA GAC GGC ACC ACC GAC ATC      1146
Met Val Leu Gln Asn Val Ser Ser Val Glu Asp Gly Thr Thr Asp Ile
295                 300                 305                 310

ACG TTC ACC TGC CCT CGC GCT GAC GGA CGC CGT GCG ATG GAG ATC TTG      1194
Thr Phe Thr Cys Pro Arg Ala Asp Gly Arg Arg Ala Met Glu Ile Leu
            315                 320                 325

AAG AAG CTT CAG GTT CAG GGC AAC TGG ACC AAT GTG CTT TAC GAC GAC      1242
Lys Lys Leu Gln Val Gln Gly Asn Trp Thr Asn Val Leu Tyr Asp Asp
            330                 335                 340

CAG GTC GGC AAA GTC TCC CTC GTG GGT GCT GGC ATG AAG TCT CAC CCA      1290
Gln Val Gly Lys Val Ser Leu Val Gly Ala Gly Met Lys Ser His Pro
            345                 350                 355

GGT GTT ACC GCA GAG TTC ATG GAA GCT CTG CGC GAT GTC AAC GTG AAC      1338
Gly Val Thr Ala Glu Phe Met Glu Ala Leu Arg Asp Val Asn Val Asn
360                 365                 370

ATC GAA TTG ATT TCC ACC TCT GAG ATC CGC ATT TCC GTG CTG ATC CGT      1386
Ile Glu Leu Ile Ser Thr Ser Glu Ile Arg Ile Ser Val Leu Ile Arg
375                 380                 385                 390

GAA GAT GAT CTG GAT GCT GCT GCA CGT GCA TTG CAT GAG CAG TTC CAG      1434
Glu Asp Asp Leu Asp Ala Ala Ala Arg Ala Leu His Glu Gln Phe Gln
                395                 400                 405

CTG GGC GGC GAA GAC GAA GCC GTC GTT TAT GCA GGC ACC GGA CGC TAA      1482
Leu Gly Gly Glu Asp Glu Ala Val Val Tyr Ala Gly Thr Gly Arg
            410                 415                 420

AGTTTTAAAG GAGTAGTTTT ACAATGACCA CCATCGCAGT TGTTGGTGCA ACCGGCCAGG   1542

TCGGCCAGGT TATGCGCACC CTTTTGGAAG AGCGCAATTT CCCAGCTGAC ACTGTTCGTT   1602

TCTTTGCTTC CCCGCGTTCC GCAGGCCGTA AGATTGAATT C                      1643
```

(2) INFORMATION FOR SEQ ID NO: 5:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ala Leu Val Val Gln Lys Tyr Gly Gly Ser Ser Leu Glu Ser Ala
  1               5                  10                 15

Glu Arg Ile Arg Asn Val Ala Glu Arg Ile Val Ala Thr Lys Lys Ala
             20                  25                 30

Gly Asn Asp Val Val Val Cys Ser Ala Met Gly Asp Thr Thr Asp
             35                  40                 45

Glu Leu Leu Glu Leu Ala Ala Val Asn Pro Val Pro Pro Ala Arg
         50                  55                 60

Glu Met Asp Met Leu Leu Thr Ala Gly Glu Arg Ile Ser Asn Ala Leu
 65                  70                  75                 80

Val Ala Met Ala Ile Glu Ser Leu Gly Ala Glu Ala Gln Ser Phe Thr
                 85                  90                 95

Gly Ser Gln Ala Gly Val Leu Thr Thr Glu Arg His Gly Asn Ala Arg
                100                 105                110

Ile Val Asp Val Thr Pro Gly Arg Val Arg Glu Ala Leu Asp Glu Gly
             115                 120                 125

Lys Ile Cys Ile Val Ala Gly Phe Gln Gly Val Asn Lys Glu Thr Arg
         130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                 165                 170                 175

Asp Gly Val Tyr Thr Ala Asp Pro Arg Ile Val Pro Asn Ala Gln Lys
             180                 185                 190

Leu Glu Lys Leu Ser Phe Glu Glu Met Leu Glu Leu Ala Ala Val Gly
         195                 200                 205

Ser Lys Ile Leu Val Leu Arg Ser Val Glu Tyr Ala Arg Ala Phe Asn
         210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                 245                 250                 255

Gly Val Ala Thr Asp Lys Ser Glu Ala Lys Val Thr Val Leu Gly Ile
             260                 265                 270

Ser Asp Lys Pro Gly Glu Ala Ala Lys Val Phe Arg Ala Leu Ala Asp
         275                 280                 285

Ala Glu Ile Asn Ile Asp Met Val Leu Gln Asn Val Ser Ser Val Glu
         290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                 325                 330                 335

Asn Val Leu Tyr Asp Asp Gln Val Gly Lys Val Ser Leu Val Gly Ala
             340                 345                 350

Gly Met Lys Ser His Pro Gly Val Thr Ala Glu Phe Met Glu Ala Leu
         355                 360                 365

Arg Asp Val Asn Val Asn Ile Glu Leu Ile Ser Thr Ser Glu Ile Arg
         370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                 405                 410                 415

Ala Gly Thr Gly Arg
                 420
```

(2) INFORMATION FOR SEQ ID NO: 6:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 964..1482

(xi) SEQUENCE DESCRIPTION: SEQ ID NO: 6:

```
TCGCGAAGTA GCACCTGTCA CTTTTGTCTC AAATATTAAA TCGAATATCA ATATACGGTC    60

TGTTTATTGG AACGCATCCC AGTGGCTGAG ACGCATCCGC TAAAGCCCCA GGAACCCTGT   120

GCAGAAAGAA ACACTCCTC  TGGCTAGGTA GACACAGTTT ATAAAGGTAG AGTTGAGCGG   180

GTAACTGTCA GCACGTAGAT CGAAAGGTGC ACAAAGGTGG CCCTGGTCGT ACAGAAATAT   240

GGCGGTTCCT CGCTTGAGAG TGCGGAACGC ATTAGAAACG TCGCTGAACG GATCGTTGCC   300

ACCAAGAAGG CTGGAAATGA TGTCGTGGTT GTCTGCTCCG CAATGGGAGA CACCACGGAT   360

GAACTTCTAG AACTTGCAGC GGCAGTGAAT CCCGTTCCGC CAGCTCGTGA ATGGATATG    420

CTCCTGACTG CTGGTGAGCG TATTTCTAAC GCTCTCGTCG CCATGGCTAT TGAGTCCCTT   480

GGCGCAGAAG CTCAATCTTT CACTGGCTCT CAGGCTGGTG TGCTCACCAC CGAGCGCCAC   540

GGAAACGCAC GCATTGTTGA CGTCACACCG GGTCGTGTGC GTGAAGCACT CGATGAGGGC   600

AAGATCTGCA TTGTTGCTGG TTTTCAGGGT GTTAATAAAG AAACCCGCGA TGTCACCACG   660

TTGGGTCGTG GTGGTTCTGA CACCACTGCA GTTGCGTTGG CAGCTGCTTT GAACGCTGAT   720

GTGTGTGAGA TTTACTCGGA CGTTGACGGT GTGTATACCG CTGACCCGCG CATCGTTCCT   780

AATGCACAGA AGCTGAAAAA GCTCAGCTTC GAAGAAATGC TGGAACTTGC TGCTGTTGGC   840

TCCAAGATTT TGGTGCTGCG CAGTGTTGAA TACGCTCGTG CATTCAATGT GCCACTTCGC   900

GTACGCTCGT CTTATAGTAA TGATCCCGGC ACTTTGATTG CCGGCTCTAT GGAGGATATT   960

CCT GTG GAA GAA GCA GTC CTT ACC GGT GTC GCA ACC GAC AAG TCC GAA  1008
    Met Glu Glu Ala Val Leu Thr Gly Val Ala Thr Asp Lys Ser Glu
     1               5                  10                  15

GCC AAA GTA ACC GTT CTG GGT ATT TCC GAT AAG CCA GGC GAG GCT GCC  1056
Ala Lys Val Thr Val Leu Gly Ile Ser Asp Lys Pro Gly Glu Ala Ala
             20                  25                  30

AAG GTT TTC CGT GCG TTG GCT GAT GCA GAA ATC AAC ATT GAC ATG GTT  1104
Lys Val Phe Arg Ala Leu Ala Asp Ala Glu Ile Asn Ile Asp Met Val
         35                  40                  45

CTG CAG AAC GTC TCC TCT GTG GAA GAC GGC ACC ACC GAC ATC ACG TTC  1152
Leu Gln Asn Val Ser Ser Val Glu Asp Gly Thr Thr Asp Ile Thr Phe
     50                  55                  60

ACC TGC CCT CGC GCT GAC GGA CGC CGT GCG ATG GAG ATC TTG AAG AAG  1200
Thr Cys Pro Arg Ala Asp Gly Arg Arg Ala Met Glu Ile Leu Lys Lys
 65                  70                  75

CTT CAG GTT CAG GGC AAC TGG ACC AAT GTG CTT TAC GAC GAC CAG GTC  1248
Leu Gln Val Gln Gly Asn Trp Thr Asn Val Leu Tyr Asp Asp Gln Val
 80                  85                  90                  95
```

```
GGC AAA GTC TCC CTC GTG GGT GCT GGC ATG AAG TCT CAC CCA GGT GTT    1296
Gly Lys Val Ser Leu Val Gly Ala Gly Met Lys Ser His Pro Gly Val
            100                 105                 110

ACC GCA GAG TTC ATG GAA GCT CTG CGC GAT GTC AAC GTG AAC ATC GAA    1344
Thr Ala Glu Phe Met Glu Ala Leu Arg Asp Val Asn Val Asn Ile Glu
            115                 120                 125

TTG ATT TCC ACC TCT GAG ATC CGC ATT TCC GTG CTG ATC CGT GAA GAT    1392
Leu Ile Ser Thr Ser Glu Ile Arg Ile Ser Val Leu Ile Arg Glu Asp
            130                 135                 140

GAT CTG GAT GCT GCT GCA CGT GCA TTG CAT GAG CAG TTC CAG CTG GGC    1440
Asp Leu Asp Ala Ala Ala Arg Ala Leu His Glu Gln Phe Gln Leu Gly
145                 150                 155

GGC GAA GAC GAA GCC GTC GTT TAT GCA GGC ACC GGA CGC TAAAGTTTTAA    1490
Gly Glu Asp Glu Ala Val Val Tyr Ala Gly Thr Gly Arg
160                 165                 170

AGGAGTAGTT TTACAATGAC CACCATCGCA GTTGTTGGTG CAACCGGCCA GGTCGGCCAG   1550

GTTATGCGCA CCCTTTTGGA AGAGCGCAAT TCCCAGCTG ACACTGTTCG TTTCTTTGCT    1610

TCCCCGCGTT CCGCAGGCCG TAAGATTGAA TTC                                1643

(2) INFORMATION FOR SEQ ID NO: 7:

(i) SEQUENCE CHARACTERISTICS:
            (A) LENGTH: 172 amino acids
            (B) TYPE: amino acid
            (D) TOPOLOGY: linear (ii) MOLECULE TYPE: protein (xi) SEQUENCE DESCRIPTION: SEQ ID NO: 7:

Met Glu Glu Ala Val Leu Thr Gly Val Ala Thr Asp Lys Ser Glu Ala
 1               5                  10                  15

Lys Val Thr Val Leu Gly Ile Ser Asp Lys Pro Gly Glu Ala Ala Lys
                20                  25                  30

Val Phe Arg Ala Leu Ala Asp Ala Glu Ile Asn Ile Asp Met Val Leu
            35                  40                  45

Gln Asn Val Ser Ser Val Glu Asp Gly Thr Thr Asp Ile Thr Phe Thr
     50                  55                  60

Cys Pro Arg Ala Asp Gly Arg Arg Ala Met Glu Ile Leu Lys Lys Leu
65                  70                  75                  80

Gln Val Gln Gly Asn Trp Thr Asn Val Leu Tyr Asp Asp Gln Val Gly
                85                  90                  95

Lys Val Ser Leu Val Gly Ala Gly Met Lys Ser His Pro Gly Val Thr
            100                 105                 110

Ala Glu Phe Met Glu Ala Leu Arg Asp Val Asn Val Asn Ile Glu Leu
        115                 120                 125

Ile Ser Thr Ser Glu Ile Arg Ile Ser Val Leu Ile Arg Glu Asp Asp
    130                 135                 140

Leu Asp Ala Ala Ala Arg Ala Leu His Glu Gln Phe Gln Leu Gly Gly
145                 150                 155                 160

Glu Asp Glu Ala Val Val Tyr Ala Gly Thr Gly Arg
                165                 170

(2) INFORMATION FOR SEQ ID NO: 8:

(i) SEQUENCE CHARACTERISTICS:
            (A) LENGTH: 23 bases
            (B) TYPE: nucleic acid
            (C) STRANDEDNESS: single
            (D) TOPOLOGY: linear
```

(ii) MOLECULE TYPE: other nucleic acid
        (A) DESCRIPTION: /desc = "synthetic DNA"

(iv) ANTI-SENSE: NO (xi) SEQUENCE DESCRIPTION: SEQ ID NO: 8:

GGATCCCCAA TCGATACCTG GAA                                         23

(2) INFORMATION FOR SEQ ID NO: 9:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: YES (xi) SEQUENCE DESCRIPTION: SEQ ID NO: 9:

CGGTTCATCG CCAAGTTTTT CTT                                         23

(2) INFORMATION FOR SEQ ID NO: 10:

(i) SEQUENCE CHARACTERISTICS:
        (A) LENGTH: 2001 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 730..1473

(xi) SEQUENCE DESCRIPTION: SEQ ID NO: 10:

```
GGATCCCCAA TCGATACCTG GAACGACAAC CTGATCAGGA TATCCAATGC CTTGAATATT     60

GACGTTGAGG AAGGAATCAC CAGCCATCTC AACTGGAAGA CCTGACGCCT GCTGAATTGG    120

ATCAGTGGCC CAATCGACCC ACCAACCAGG TTGGCTATTA CCGGCGATAT CAAAAACAAC    180

TCGCGTGAAC GTTTCGTGCT CGGCAACGCG GATGCCAGCG ATCGACATAT CGGAGTCACC    240

AACTTGAGCC TGCTGCTTCT GATCCATCGA CGGGGAACCC AACGGCGGCA AGCAGTGGG     300

GGAAGGGGAG TTGGTGGACT CTGAATCAGT GGGCTCTGAA GTGGTAGGCG ACGGGGCAGC    360

ATCTGAAGGC GTGCGAGTTG TGGTGACCGG GTTAGCGGTT TCAGTTTCTG TCACAACTGG    420

AGCAGGACTA GCAGAGGTTG TAGGCGTTGA GCCGCTTCCA TCACAAGCAC TTAAAAGTAA    480

AGAGGCGGAA ACCACAAGCG CCAAGGAACT ACCTGCGGAA CGGGCGGTGA AGGGCAACTT    540

AAGTCTCATA TTTCAAACAT AGTTCCACCT GTGTGATTAA TCTCCAGAAC GGAACAAACT    600

GATGAACAAT CGTTAACAAC ACAGACCAAA ACGGTCAGTT AGGTATGGAT ATCAGCACCT    660

TCTGAATGGG TACGTCTAGA CTGGTGGGCG TTTGAAAAAC TCTTCGCCCC ACGAAAATGA    720

AGGAGCATA ATG GGA ATC AAG GTT GGC GTT CTC GGA GCC AAA GGC CGT        768
          Met Gly Ile Lys Val Gly Val Leu Gly Ala Lys Gly Arg
            1               5                  10

GTT GGT CAA ACT ATT GTG GCA GCA GTC AAT GAG TCC GAC GAT CTG GAG      816
Val Gly Gln Thr Ile Val Ala Ala Val Asn Glu Ser Asp Asp Leu Glu
```

```
                    15                    20                    25
CTT GTT GCA GAG ATC GGC GTC GAC GAT GAT TTG AGC CTT CTG GTA GAC        864
Leu Val Ala Glu Ile Gly Val Asp Asp Asp Leu Ser Leu Leu Val Asp
 30                    35                    40                    45

AAC GGC GCT GAA GTT GTC GTT GAC TTC ACC ACT CCT AAC GCT GTG ATG        912
Asn Gly Ala Glu Val Val Val Asp Phe Thr Thr Pro Asn Ala Val Met
                    50                    55                    60

GGC AAC CTG GAG TTC TGC ATC AAC AAC GGC ATT TCT GCG GTT GTT GGA        960
Gly Asn Leu Glu Phe Cys Ile Asn Asn Gly Ile Ser Ala Val Val Gly
                65                    70                    75

ACC ACG GGC TTC GAT GAT GCT CGT TTG GAG CAG GTT CGC GCC TGG CTT       1008
Thr Thr Gly Phe Asp Asp Ala Arg Leu Glu Gln Val Arg Ala Trp Leu
            80                    85                    90

GAA GGA AAA GAC AAT GTC GGT GTT CTG ATC GCA CCT AAC TTT GCT ATC       1056
Glu Gly Lys Asp Asn Val Gly Val Leu Ile Ala Pro Asn Phe Ala Ile
        95                   100                   105

TCT GCG GTG TTG ACC ATG GTC TTT TCC AAG CAG GCT GCC CGC TTC TTC       1104
Ser Ala Val Leu Thr Met Val Phe Ser Lys Gln Ala Ala Arg Phe Phe
110                   115                   120                   125

GAA TCA GCT GAA GTT ATT GAG CTG CAC CAC CCC AAC AAG CTG GAT GCA       1152
Glu Ser Ala Glu Val Ile Glu Leu His His Pro Asn Lys Leu Asp Ala
                    130                   135                   140

CCT TCA GGC ACC GCG ATC CAC ACT GCT CAG GGC ATT GCT GCG GCA CGC       1200
Pro Ser Gly Thr Ala Ile His Thr Ala Gln Gly Ile Ala Ala Ala Arg
                145                   150                   155

AAA GAA GCA GGC ATG GAC GCA CAG CCA GAT GCG ACC GAG CAG GCA CTT       1248
Lys Glu Ala Gly Met Asp Ala Gln Pro Asp Ala Thr Glu Gln Ala Leu
            160                   165                   170

GAG GGT TCC CGT GGC GCA AGC GTA GAT GGA ATC CCA GTT CAC GCA GTC       1296
Glu Gly Ser Arg Gly Ala Ser Val Asp Gly Ile Pro Val His Ala Val
        175                   180                   185

CGC ATG TCC GGC ATG GTT GCT CAC GAG CAA GTT ATC TTT GGC ACC CAG       1344
Arg Met Ser Gly Met Val Ala His Glu Gln Val Ile Phe Gly Thr Gln
190                   195                   200                   205

GGT CAG ACC TTG ACC ATC AAG CAG GAC TCC TAT GAT CGC AAC TCA TTT       1392
Gly Gln Thr Leu Thr Ile Lys Gln Asp Ser Tyr Asp Arg Asn Ser Phe
                    210                   215                   220

GCA CCA GGT GTC TTG GTG GGT GTG CGC AAC ATT GCA CAG CAC CCA GGC       1440
Ala Pro Gly Val Leu Val Gly Val Arg Asn Ile Ala Gln His Pro Gly
                225                   230                   235

CTA GTC GTA GGA CTT GAG CAT TAC CTA GGC CTG TAAAGGCTCA TTTCAGCAGC     1493
Leu Val Val Gly Leu Glu His Tyr Leu Gly Leu
            240                   245

GGGTGGAATT TTTTAAAAGG AGCGTTTAAA GGCTGTGGCC GAACAAGTTA AATTGAGCGT     1553

GGAGTTGATA GCGTGCAGTT CTTTTACTCC ACCCGCTGAT GTTGAGTGGT CAACTGATGT     1613

TGAGGGCGCG GAAGCACTCG TCGAGTTTGC GGGTCGTGCC TGCTACGAAA CTTTTGATAA     1673

GCCGAACCCT CGAACTGCTT CCAATGCTGC GTATCTGCGC CACATCATGG AAGTGGGGCA     1733

CACTGCTTTG CTTGAGCATG CCAATGCCAC GATGTATATC CGAGGCATTT CTCGGTCCGC     1793

GACCCATGAA TTGGTCCGAC ACCGCCATTT TCCTTCTCT CAACTGTCTC AGCGTTTCGT      1853

GCACAGCGGA GAATCGGAAG TAGTGGTGCC CACTCTCATC GATGAAGATC CGCAGTTGCG     1913

TGAACTTTTC ATGCACGCCA TGGATGAGTC TCGGTTCGCT TTCAATGAGC TGCTTAATGC     1973

GCTGGAAGAA AAACTTGGCG ATGAACCG                                       2001
```

(2) INFORMATION FOR SEQ ID NO: 11:

(i) SEQUENCE CHARACTERISTICS:

(A) LENGTH: 248 amino acids
(B) TYPE: amino acid
(D) TOPOLOGY: linear (ii) MOLECULE TYPE: protein (xi) SEQUENCE DESCRIPTION: SEQ ID NO: 11:

```
Met Gly Ile Lys Val Gly Val Leu Gly Ala Lys Gly Arg Val Gly Gln
 1               5                  10                  15
Thr Ile Val Ala Ala Val Asn Glu Ser Asp Asp Leu Glu Leu Val Ala
                20                  25                  30
Glu Ile Gly Val Asp Asp Leu Ser Leu Leu Val Asp Asn Gly Ala
                35                  40                  45
Glu Val Val Asp Phe Thr Thr Pro Asn Ala Val Met Gly Asn Leu
 50                  55                  60
Glu Phe Cys Ile Asn Asn Gly Ile Ser Ala Val Val Gly Thr Thr Gly
 65                  70                  75                  80
Phe Asp Asp Ala Arg Leu Glu Gln Val Arg Ala Trp Leu Glu Gly Lys
                85                  90                  95
Asp Asn Val Gly Val Leu Ile Ala Pro Asn Phe Ala Ile Ser Ala Val
                100                 105                 110
Leu Thr Met Val Phe Ser Lys Gln Ala Ala Arg Phe Phe Glu Ser Ala
                115                 120                 125
Glu Val Ile Glu Leu His His Pro Asn Lys Leu Asp Ala Pro Ser Gly
                130                 135                 140
Thr Ala Ile His Thr Ala Gln Gly Ile Ala Ala Ala Arg Lys Glu Ala
145                 150                 155                 160
Gly Met Asp Ala Gln Pro Asp Ala Thr Glu Gln Ala Leu Glu Gly Ser
                165                 170                 175
Arg Gly Ala Ser Val Asp Gly Ile Pro Val His Ala Val Arg Met Ser
                180                 185                 190
Gly Met Val Ala His Glu Gln Val Ile Phe Gly Thr Gln Gly Gln Thr
                195                 200                 205
Leu Thr Ile Lys Gln Asp Ser Tyr Asp Arg Asn Ser Phe Ala Pro Gly
                210                 215                 220
Val Leu Val Gly Val Arg Asn Ile Ala Gln His Pro Gly Leu Val Val
225                 230                 235                 240
Gly Leu Glu His Tyr Leu Gly Leu
                245
```

(2) INFORMATION FOR SEQ ID NO: 12:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: NO (xi) SEQUENCE DESCRIPTION: SEQ ID NO: 12:

GTCGACGGAT CGCAAATGGC AAC                                              23

(2) INFORMATION FOR SEQ ID NO: 13:

(i) SEQUENCE CHARACTERISTICS:
        (A) LENGTH: 23 bases
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: YES (xi) SEQUENCE DESCRIPTION: SEQ ID NO: 13:

GGATCCTTGA GCACCTTGCG CAG                                          23

(2) INFORMATION FOR SEQ ID NO: 14:

(i) SEQUENCE CHARACTERISTICS:
        (A) LENGTH: 1411 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 311..1213

(xi) SEQUENCE DESCRIPTION: SEQ ID NO: 14:

CTCTCGATAT CGAGAGAGAA GCAGCGCCAC GGTTTTTCGG TGATTTTGAG ATTGAAACTT    60

TGGCAGACGG ATCGCAAATG GCAACAAGCC CGTATGTCAT GGACTTTTAA CGCAAAGCTC   120

ACACCCACGA GCTAAAAATT CATATAGTTA AGACAACATT TTTGGCTGTA AAAGACAGCC   180

GTAAAAACCT CTTGCTCATG TCAATTGTTC TTATCGGAAT GTGGCTTGGG CGATTGTTAT   240

GCAAAGTTG  TTAGGTTTTT TGCGGGGTTG TTTAACCCCC AAATGAGGGA AGAAGGTAAC   300
```

| | | | | | | | | | | | | |
|---|---|---|---|---|---|---|---|---|---|---|---|---|
| CTTGAACTCT | ATG | AGC | ACA | GGT | TTA | ACA | GCT | AAG | ACC | GGA | GTA | GAG CAC | 349 |
| | Met | Ser | Thr | Gly | Leu | Thr | Ala | Lys | Thr | Gly | Val | Glu His | |
| | 1 | | | 5 | | | | | 10 | | | | |

```
TTC GGC ACC GTT GGA GTA GCA ATG GTT ACT CCA TTC ACG GAA TCC GGA    397
Phe Gly Thr Val Gly Val Ala Met Val Thr Pro Phe Thr Glu Ser Gly
 15                  20                  25

GAC ATC GAT ATC GCT GCT GGC CGC GAA GTC GCG GCT TAT TTG GTT GAT    445
Asp Ile Asp Ile Ala Ala Gly Arg Glu Val Ala Ala Tyr Leu Val Asp
 30                  35                  40                  45

AAG GGC TTG GAT TCT TTG GTT CTC GCG GGC ACC ACT GGT GAA TCC CCA    493
Lys Gly Leu Asp Ser Leu Val Leu Ala Gly Thr Thr Gly Glu Ser Pro
                 50                  55                  60

ACG ACA ACC GCC GCT GAA AAA CTA GAA CTG CTC AAG GCC GTT CGT GAG    541
Thr Thr Thr Ala Ala Glu Lys Leu Glu Leu Leu Lys Ala Val Arg Glu
             65                  70                  75

GAA GTT GGG GAT CGG GCG AAC GTC ATC GCC GGT GTC GGA ACC AAC AAC    589
Glu Val Gly Asp Arg Ala Asn Val Ile Ala Gly Val Gly Thr Asn Asn
         80                  85                  90

ACG CGG ACA TCT GTG GAA CTT GCG GAA GCT GCT GCT TCT GCT GGC GCA    637
Thr Arg Thr Ser Val Glu Leu Ala Glu Ala Ala Ala Ser Ala Gly Ala
     95                 100                 105

GAC GGC CTT TTA GTT GTA ACT CCT TAT TAC TCC AAG CCG AGC CAA GAG    685
Asp Gly Leu Leu Val Val Thr Pro Tyr Tyr Ser Lys Pro Ser Gln Glu
110                 115                 120                 125

GGA TTG CTG GCG CAC TTC GGT GCA ATT GCT GCA GCA ACA GAG GTT CCA    733
Gly Leu Leu Ala His Phe Gly Ala Ile Ala Ala Ala Thr Glu Val Pro
                130                 135                 140
```

```
ATT TGT CTC TAT GAC ATT CCT GGT CGG TCA GGT ATT CCA ATT GAG TCT       781
Ile Cys Leu Tyr Asp Ile Pro Gly Arg Ser Gly Ile Pro Ile Glu Ser
            145                 150                 155

GAT ACC ATG AGA CGC CTG AGT GAA TTA CCT ACG ATT TTG GCG GTC AAG       829
Asp Thr Met Arg Arg Leu Ser Glu Leu Pro Thr Ile Leu Ala Val Lys
            160                 165                 170

GAC GCC AAG GGT GAC CTC GTT GCA GCC ACG TCA TTG ATC AAA GAA ACG       877
Asp Ala Lys Gly Asp Leu Val Ala Ala Thr Ser Leu Ile Lys Glu Thr
        175                 180                 185

GGA CTT GCC TGG TAT TCA GGC GAT GAC CCA CTA AAC CTT GTT TGG CTT       925
Gly Leu Ala Trp Tyr Ser Gly Asp Asp Pro Leu Asn Leu Val Trp Leu
190                 195                 200                 205

GCT TTG GGC GGA TCA GGT TTC ATT TCC GTA ATT GGA CAT GCA GCC CCC       973
Ala Leu Gly Gly Ser Gly Phe Ile Ser Val Ile Gly His Ala Ala Pro
                210                 215                 220

ACA GCA TTA CGT GAG TTG TAC ACA AGC TTC GAG GAA GGC GAC CTC GTC      1021
Thr Ala Leu Arg Glu Leu Tyr Thr Ser Phe Glu Glu Gly Asp Leu Val
                    225                 230                 235

CGT GCG CGG GAA ATC AAC GCC AAA CTA TCA CCG CTG GTA GCT GCC CAA      1069
Arg Ala Arg Glu Ile Asn Ala Lys Leu Ser Pro Leu Val Ala Ala Gln
        240                 245                 250

GGT CGC TTG GGT GGA GTC AGC TTG GCA AAA GCT GCT CTG CGT CTG CAG      1117
Gly Arg Leu Gly Gly Val Ser Leu Ala Lys Ala Ala Leu Arg Leu Gln
255                 260                 265

GGC ATC AAC GTA GGA GAT CCT CGA CTT CCA ATT ATG GCT CCA AAT GAG      1165
Gly Ile Asn Val Gly Asp Pro Arg Leu Pro Ile Met Ala Pro Asn Glu
270                 275                 280                 285

CAG GAA CTT GAG GCT CTC CGA GAA GAC ATG AAA AAA GCT GGA GTT CTA      1213
Gln Glu Leu Glu Ala Leu Arg Glu Asp Met Lys Lys Ala Gly Val Leu
                290                 295                 300

TAAATATGAA TGATTCCCGA AATCGCGGCC GGAAGGTTAC CCGCAAGGCG GCCCACCAGA    1273

AGCTGGTCAG GAAACCATC TGGATACCCC TGTCTTTCAG GCACCAGATG CTTCCTCTAA     1333

CCAGAGCGCT GTAAAAGCTG AGACCGCCGG AAACGACAAT CGGGATGCTG CGCAAGGTGC    1393

TCAAGGATCC CAACATTC                                                  1411

(2) INFORMATION FOR SEQ ID NO: 15:

(i) SEQUENCE CHARACTERISTICS:
        (A) LENGTH: 301 amino acids
        (B) TYPE: amino acid
        (D) TOPOLOGY: linear (ii) MOLECULE TYPE: protein (xi) SEQUENCE DESCRIPTION: SEQ ID NO: 15:

Met Ser Thr Gly Leu Thr Ala Lys Thr Gly Val Glu His Phe Gly Thr
 1               5                  10                  15

Val Gly Val Ala Met Val Thr Pro Phe Thr Glu Ser Gly Asp Ile Asp
                20                  25                  30

Ile Ala Ala Gly Arg Glu Val Ala Ala Tyr Leu Val Asp Lys Gly Leu
            35                  40                  45

Asp Ser Leu Val Leu Ala Gly Thr Thr Gly Glu Ser Pro Thr Thr Thr
        50                  55                  60

Ala Ala Glu Lys Leu Glu Leu Leu Lys Ala Val Arg Glu Glu Val Gly
    65                  70                  75                  80

Asp Arg Ala Asn Val Ile Ala Gly Val Gly Thr Asn Asn Thr Arg Thr
                85                  90                  95

Ser Val Glu Leu Ala Glu Ala Ala Ala Ser Ala Gly Ala Asp Gly Leu
```

```
            100                 105                 110
Leu Val Val Thr Pro Tyr Tyr Ser Lys Pro Ser Gln Glu Gly Leu Leu
        115                 120                 125

Ala His Phe Gly Ala Ile Ala Ala Thr Glu Val Pro Ile Cys Leu
130                 135                 140

Tyr Asp Ile Pro Gly Arg Ser Gly Ile Pro Ile Glu Ser Asp Thr Met
145                 150                 155                 160

Arg Arg Leu Ser Glu Leu Pro Thr Ile Leu Ala Val Lys Asp Ala Lys
                165                 170                 175

Gly Asp Leu Val Ala Ala Thr Ser Leu Ile Lys Glu Thr Gly Leu Ala
            180                 185                 190

Trp Tyr Ser Gly Asp Asp Pro Leu Asn Leu Val Trp Leu Ala Leu Gly
        195                 200                 205

Gly Ser Gly Phe Ile Ser Val Ile Gly His Ala Ala Pro Thr Ala Leu
    210                 215                 220

Arg Glu Leu Tyr Thr Ser Phe Glu Glu Gly Asp Leu Val Arg Ala Arg
225                 230                 235                 240

Glu Ile Asn Ala Lys Leu Ser Pro Leu Val Ala Ala Gln Gly Arg Leu
                245                 250                 255

Gly Gly Val Ser Leu Ala Lys Ala Ala Leu Arg Leu Gln Gly Ile Asn
            260                 265                 270

Val Gly Asp Pro Arg Leu Pro Ile Met Ala Pro Asn Glu Gln Glu Leu
        275                 280                 285

Glu Ala Leu Arg Glu Asp Met Lys Lys Ala Gly Val Leu
    290                 295                 300

(2) INFORMATION FOR SEQ ID NO: 16:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: NO (xi) SEQUENCE DESCRIPTION: SEQ ID NO: 16:

GTGGAGCCGA CCATTCCGCG AGG                                            23

(2) INFORMATION FOR SEQ ID NO: 17:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iv) ANTI-SENSE: YES (xi) SEQUENCE DESCRIPTION: SEQ ID NO: 17:

CCAAAACCGC CCTCCACGGC GAA                                            23

(2) INFORMATION FOR SEQ ID NO: 18:

(i) SEQUENCE CHARACTERISTICS:
        (A) LENGTH: 3579 base pairs
        (B) TYPE: nucleic acid
```

-continued

```
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
         (A) ORGANISM: Brevibacterium lactofermentum
         (B) STRAIN: ATCC 13869

(ix) FEATURE:
         (A) NAME/KEY: CDS
         (B) LOCATION: 533..2182

(ix) FEATURE:
         (A) NAME/KEY: CDS
         (B) LOCATION: 2188..3522

(xi) SEQUENCE DESCRIPTION: SEQ ID NO: 18:

GTGGAGCCGA CCATTCCGCG AGGCTGCACT GCAACGAGGT CGTAGTTTTG GTACATGGCT        60

TCTGGCCAGT TCATGGATTG GCTGCCGAAG AAGCTATAGG CATCGCACCA GGGCCACCGA       120

GTTACCGAAG ATGGTGCCGT GCTTTTCGCC TTGGGCAGGG ACCTTGACAA AGCCCACGCT       180

GATATCGCCA AGTGAGGGAT CAGAATAGTG CATGGGCACG TCGATGCTGC CACATTGAGC       240

GGAGGCAATA TCTACCTGAG GTGGGCATTC TTCCCAGCGG ATGTTTTCTT GCGCTGCTGC       300

AGTGGGCATT GATACCAAAA AGGGGCTAAG CGCAGTCGAG GCGGCAAGAA CTGCTACTAC       360

CCTTTTTATT GTCGAACGGG GCATTACGGC TCCAAGGACG TTTGTTTTCT GGGTCAGTTA       420

CCCCAAAAAG CATATACAGA GACCAATGAT TTTTCATTAA AAAGGCAGGG ATTTGTTATA       480

AGTATGGGTC GTATTCTGTG CGACGGGTGT ACCTCGGCTA GAATTTCTCC CC ATG          535
                                                         Met
                                                         1

ACA CCA GCT GAT CTC GCA ACA TTG ATT AAA GAG ACC GCG GTA GAG GTT        583
Thr Pro Ala Asp Leu Ala Thr Leu Ile Lys Glu Thr Ala Val Glu Val
        5                   10                  15

TTG ACC TCC CGC GAG CTC GAT ACT TCT GTT CTT CCG GAG CAG GTA GTT        631
Leu Thr Ser Arg Glu Leu Asp Thr Ser Val Leu Pro Glu Gln Val Val
    20                  25                  30

GTG GAG CGT CCG CGT AAC CCA GAG CAC GGC GAT TAC GCC ACC AAC ATT        679
Val Glu Arg Pro Arg Asn Pro Glu His Gly Asp Tyr Ala Thr Asn Ile
35                  40                  45

GCA TTG CAG GTG GCT AAA AAG GTC GGT CAG AAC CCT CGG GAT TTG GCT        727
Ala Leu Gln Val Ala Lys Lys Val Gly Gln Asn Pro Arg Asp Leu Ala
    50                  55                  60                  65

ACC TGG CTG GCA GAG GCA TTG GCT GCA GAT GAC GCC ATT GAT TCT GCT        775
Thr Trp Leu Ala Glu Ala Leu Ala Ala Asp Asp Ala Ile Asp Ser Ala
            70                  75                  80

GAA ATT GCT GGC CCA GGC TTT TTG AAC ATT CGC CTT GCT GCA GCA GCA        823
Glu Ile Ala Gly Pro Gly Phe Leu Asn Ile Arg Leu Ala Ala Ala Ala
                85                  90                  95

CAG GGT GAA ATT GTG GCC AAG ATT CTG GCA CAG GGC GAG ACT TTC GGA        871
Gln Gly Glu Ile Val Ala Lys Ile Leu Ala Gln Gly Glu Thr Phe Gly
            100                 105                 110

AAC TCC GAT CAC CTT TCC CAC TTG GAC GTG AAC CTC GAG TTC GTT TCT        919
Asn Ser Asp His Leu Ser His Leu Asp Val Asn Leu Glu Phe Val Ser
115                 120                 125

GCA AAC CCA ACC GGA CCT ATT CAC CTT GGC GGA ACC CGC TGG GCT GCC        967
Ala Asn Pro Thr Gly Pro Ile His Leu Gly Gly Thr Arg Trp Ala Ala
    130                 135                 140                 145

GTG GGT GAC TCT TTG GGT CGT GTG CTG GAG GCT TCC GGC GCG AAA GTG       1015
Val Gly Asp Ser Leu Gly Arg Val Leu Glu Ala Ser Gly Ala Lys Val
            150                 155                 160
```

-continued

```
ACC CGC GAA TAC TAC TTC AAC GAT CAC GGT CGC CAG ATC GAT CGT TTC      1063
Thr Arg Glu Tyr Tyr Phe Asn Asp His Gly Arg Gln Ile Asp Arg Phe
        165                 170                 175

GCT TTG TCC CTT CTT GCA GCG GCG AAG GGC GAG CCA ACG CCA GAA GAC      1111
Ala Leu Ser Leu Leu Ala Ala Ala Lys Gly Glu Pro Thr Pro Glu Asp
            180                 185                 190

GGT TAT GGC GGC GAA TAC ATT AAG GAA ATT GCG GAG GCA ATC GTC GAA      1159
Gly Tyr Gly Gly Glu Tyr Ile Lys Glu Ile Ala Glu Ala Ile Val Glu
195                 200                 205

AAG CAT CCT GAA GCG TTG GCT TTG GAG CCT GCC GCA ACC CAG GAG CTT      1207
Lys His Pro Glu Ala Leu Ala Leu Glu Pro Ala Ala Thr Gln Glu Leu
210                 215                 220                 225

TTC CGC GCT GAA GGC GTG GAG ATG ATG TTC GAG CAC ATC AAA TCT TCC      1255
Phe Arg Ala Glu Gly Val Glu Met Met Phe Glu His Ile Lys Ser Ser
                230                 235                 240

CTG CAT GAG TTC GGC ACC GAT TTC GAT GTC TAC TAC CAC GAG AAC TCC      1303
Leu His Glu Phe Gly Thr Asp Phe Asp Val Tyr Tyr His Glu Asn Ser
            245                 250                 255

CTG TTC GAG TCC GGT GCG GTG GAC AAG GCC GTG CAG GTG CTG AAG GAC      1351
Leu Phe Glu Ser Gly Ala Val Asp Lys Ala Val Gln Val Leu Lys Asp
        260                 265                 270

AAC GGC AAC CTG TAC GAA AAC GAG GGC GCT TGG TGG CTG CGT TCC ACC      1399
Asn Gly Asn Leu Tyr Glu Asn Glu Gly Ala Trp Trp Leu Arg Ser Thr
275                 280                 285

GAA TTC GGC GAT GAC AAA GAC CGC GTG GTG ATC AAG TCT GAC GGC GAC      1447
Glu Phe Gly Asp Asp Lys Asp Arg Val Val Ile Lys Ser Asp Gly Asp
290                 295                 300                 305

GCA GCC TAC ATC GCT GGC GAT ATC GCG TAC GTG GCT GAT AAG TTC TCC      1495
Ala Ala Tyr Ile Ala Gly Asp Ile Ala Tyr Val Ala Asp Lys Phe Ser
                310                 315                 320

CGC GGA CAC AAC CTA AAC ATC TAC ATG TTG GGT GCT GAC CAC CAT GGT      1543
Arg Gly His Asn Leu Asn Ile Tyr Met Leu Gly Ala Asp His His Gly
            325                 330                 335

TAC ATC GCG CGC CTG AAG GCA GCG GCG GCG GCA CTT GGC TAC AAG CCA      1591
Tyr Ile Ala Arg Leu Lys Ala Ala Ala Ala Ala Leu Gly Tyr Lys Pro
        340                 345                 350

GAA GGC GTT GAA GTC CTG ATT GGC CAG ATG GTG AAC CTG CTT CGC GAC      1639
Glu Gly Val Glu Val Leu Ile Gly Gln Met Val Asn Leu Leu Arg Asp
355                 360                 365

GGC AAG GCA GTG CGT ATG TCC AAG CGT GCA GGC ACC GTG GTC ACC CTA      1687
Gly Lys Ala Val Arg Met Ser Lys Arg Ala Gly Thr Val Val Thr Leu
370                 375                 380                 385

GAT GAC CTC GTT GAA GCA ATC GGC ATC GAT GCG GCG CGT TAC TCC CTG      1735
Asp Asp Leu Val Glu Ala Ile Gly Ile Asp Ala Ala Arg Tyr Ser Leu
                390                 395                 400

ATC CGT TCC TCC GTG GAT TCT TCC CTG GAT ATC GAT CTC GGC CTG TGG      1783
Ile Arg Ser Ser Val Asp Ser Ser Leu Asp Ile Asp Leu Gly Leu Trp
            405                 410                 415

GAA TCC CAG TCC TCC GAC AAC CCT GTG TAC TAC GTG CAG TAC GGA CAC      1831
Glu Ser Gln Ser Ser Asp Asn Pro Val Tyr Tyr Val Gln Tyr Gly His
        420                 425                 430

GCT CGT CTG TGC TCC ATC GCG CGC AAG GCA GAG ACC TTG GGT GTC ACC      1879
Ala Arg Leu Cys Ser Ile Ala Arg Lys Ala Glu Thr Leu Gly Val Thr
435                 440                 445

GAG GAA GGC GCA GAC CTA TCT CTA CTG ACC CAC GAC CGC GAA GGC GAT      1927
Glu Glu Gly Ala Asp Leu Ser Leu Leu Thr His Asp Arg Glu Gly Asp
450                 455                 460                 465

CTC ATC CGC ACA CTC GGA GAG TTC CCA GCA GTG GTG AAG GCT GCC GCT      1975
Leu Ile Arg Thr Leu Gly Glu Phe Pro Ala Val Val Lys Ala Ala Ala
            470                 475                 480
```

-continued

```
GAC CTA CGT GAA CCA CAC CGC ATT GCC CGC TAT GCT GAG GAA TTA GCT    2023
Asp Leu Arg Glu Pro His Arg Ile Ala Arg Tyr Ala Glu Glu Leu Ala
            485                 490                 495

GGA ACT TTC CAC CGC TTC TAC GAT TCC TGC CAC ATC CTT CCA AAG GTT    2071
Gly Thr Phe His Arg Phe Tyr Asp Ser Cys His Ile Leu Pro Lys Val
        500                 505                 510

GAT GAG GAT ACG GCA CCA ATC CAC ACA GCA CGT CTG GCA CTT GCA GCA    2119
Asp Glu Asp Thr Ala Pro Ile His Thr Ala Arg Leu Ala Leu Ala Ala
    515                 520                 525

GCA ACC CGC CAG ACC CTC GCT AAC GCC CTG CAC CTG GTT GGC GTT TCC    2167
Ala Thr Arg Gln Thr Leu Ala Asn Ala Leu His Leu Val Gly Val Ser
530                 535                 540                 545

GCA CCG GAG AAG ATG TAACA ATG GCT ACA GTT GAA AAT TTC AAT GAA      2214
Ala Pro Glu Lys Met       Met Ala Thr Val Glu Asn Phe Asn Glu
                550         1               5

CTT CCC GCA CAC GTA TGG CCA CGC AAT GCC GTG CGC CAA GAA GAC GGC    2262
Leu Pro Ala His Val Trp Pro Arg Asn Ala Val Arg Gln Glu Asp Gly
 10              15                  20                  25

GTT GTC ACC GTC GCT GGT GTG CCT CTG CCT GAC CTC GCT GAA GAA TAC    2310
Val Val Thr Val Ala Gly Val Pro Leu Pro Asp Leu Ala Glu Glu Tyr
                 30                  35                  40

GGA ACC CCA CTG TTC GTA GTC GAC GAG GAC GAT TTC CGT TCC CGC TGT    2358
Gly Thr Pro Leu Phe Val Val Asp Glu Asp Asp Phe Arg Ser Arg Cys
             45                  50                  55

CGC GAC ATG GCT ACC GCA TTC GGT GGA CCA GGC AAT GTG CAC TAC GCA    2406
Arg Asp Met Ala Thr Ala Phe Gly Gly Pro Gly Asn Val His Tyr Ala
         60                  65                  70

TCT AAA GCG TTC CTG ACC AAG ACC ATT GCA CGT TGG GTT GAT GAA GAG    2454
Ser Lys Ala Phe Leu Thr Lys Thr Ile Ala Arg Trp Val Asp Glu Glu
 75                  80                  85

GGG CTG GCA CTG GAC ATT GCA TCC ATC AAC GAA CTG GGC ATT GCC CTG    2502
Gly Leu Ala Leu Asp Ile Ala Ser Ile Asn Glu Leu Gly Ile Ala Leu
 90                  95                 100                 105

GCC GCT GGT TTC CCC GCC AGC CGT ATC ACC GCG CAC GGC AAC AAC AAA    2550
Ala Ala Gly Phe Pro Ala Ser Arg Ile Thr Ala His Gly Asn Asn Lys
                110                 115                 120

GGC GTA GAG TTC CTG CGC GCG TTG GTT CAA AAC GGT GTG GGA CAC GTG    2598
Gly Val Glu Phe Leu Arg Ala Leu Val Gln Asn Gly Val Gly His Val
            125                 130                 135

GTG CTG GAC TCC GCA CAG GAA CTA GAA CTG TTG GAT TAC GTT GCC GCT    2646
Val Leu Asp Ser Ala Gln Glu Leu Glu Leu Leu Asp Tyr Val Ala Ala
        140                 145                 150

GGT GAA GGC AAG ATT CAG GAC GTG TTG ATC CGC GTA AAG CCA GGC ATC    2694
Gly Glu Gly Lys Ile Gln Asp Val Leu Ile Arg Val Lys Pro Gly Ile
    155                 160                 165

GAA GCA CAC ACC CAC GAG TTC ATC GCC ACT AGC CAC GAA GAC CAG AAG    2742
Glu Ala His Thr His Glu Phe Ile Ala Thr Ser His Glu Asp Gln Lys
170                 175                 180                 185

TTC GGA TTC TCC CTG GCA TCC GGT TCC GCA TTC GAA GCA GCA AAA GCC    2790
Phe Gly Phe Ser Leu Ala Ser Gly Ser Ala Phe Glu Ala Ala Lys Ala
                190                 195                 200

GCC AAC AAC GCA GAA AAC CTG AAC CTG GTT GGC CTG CAC TGC CAC GTT    2838
Ala Asn Asn Ala Glu Asn Leu Asn Leu Val Gly Leu His Cys His Val
            205                 210                 215

GGT TCC CAG GTG TTC GAC GCC GAA GGC TTC AAG CTG GCA GCA GAA CGC    2886
Gly Ser Gln Val Phe Asp Ala Glu Gly Phe Lys Leu Ala Ala Glu Arg
        220                 225                 230

GTG TTG GGC CTG TAC TCA CAG ATC CAC AGC GAA CTG GGC GTT GCC CTT    2934
Val Leu Gly Leu Tyr Ser Gln Ile His Ser Glu Leu Gly Val Ala Leu
    235                 240                 245
```

```
CCT GAA CTG GAT CTC GGT GGC GGA TAC GGC ATT GCC TAT ACC GCA GCT    2982
Pro Glu Leu Asp Leu Gly Gly Gly Tyr Gly Ile Ala Tyr Thr Ala Ala
250                 255                 260                 265

GAA GAA CCA CTC AAC GTC GCA GAA GTT GCC TCC GAC CTG CTC ACC GCA    3030
Glu Glu Pro Leu Asn Val Ala Glu Val Ala Ser Asp Leu Leu Thr Ala
                270                 275                 280

GTC GGA AAA ATG GCA GCG GAA CTA GGC ATC GAC GCA CCA ACC GTG CTT    3078
Val Gly Lys Met Ala Ala Glu Leu Gly Ile Asp Ala Pro Thr Val Leu
            285                 290                 295

GTT GAG CCC GGC CGC GCT ATC GCA GGC CCC TCC ACC GTG ACC ATC TAC    3126
Val Glu Pro Gly Arg Ala Ile Ala Gly Pro Ser Thr Val Thr Ile Tyr
        300                 305                 310

GAA GTC GGC ACC ACC AAA GAC GTC CAC GTA GAC GAC GAC AAA ACC CGC    3174
Glu Val Gly Thr Thr Lys Asp Val His Val Asp Asp Asp Lys Thr Arg
    315                 320                 325

CGT TAC ATC GCC GTG GAC GGA GGC ATG TCC GAC AAC ATC CGC CCA GCA    3222
Arg Tyr Ile Ala Val Asp Gly Gly Met Ser Asp Asn Ile Arg Pro Ala
330                 335                 340                 345

CTC TAC GGC TCC GAA TAC GAC GCC CGC GTA GTA TCC CGC TTC GCC GAA    3270
Leu Tyr Gly Ser Glu Tyr Asp Ala Arg Val Val Ser Arg Phe Ala Glu
                350                 355                 360

GGA GAC CCA GTA AGC ACC CGC ATC GTG GGC TCC CAC TGC GAA TCC GGC    3318
Gly Asp Pro Val Ser Thr Arg Ile Val Gly Ser His Cys Glu Ser Gly
                365                 370                 375

GAT ATC CTG ATC AAC GAT GAA ATC TAC CCA TCT GAC ATC ACC AGC GGC    3366
Asp Ile Leu Ile Asn Asp Glu Ile Tyr Pro Ser Asp Ile Thr Ser Gly
            380                 385                 390

GAC TTC CTT GCA CTC GCA GCC ACC GGC GCA TAC TGC TAC GCC ATG AGC    3414
Asp Phe Leu Ala Leu Ala Ala Thr Gly Ala Tyr Cys Tyr Ala Met Ser
        395                 400                 405

TCC CGC TAC AAC GCC TTC ACA CGG CCC GCC GTC GTG TCC GTC CGC GCT    3462
Ser Arg Tyr Asn Ala Phe Thr Arg Pro Ala Val Val Ser Val Arg Ala
410                 415                 420                 425

GGC AGC TCC CGC CTC ATG CTG CGC CGC GAA ACG CTC GAC GAC ATC CTC    3510
Gly Ser Ser Arg Leu Met Leu Arg Arg Glu Thr Leu Asp Asp Ile Leu
                430                 435                 440

TCA CTA GAG GCA TAACGCTTTT CGACGCCTGA CCCCGCCCTT CACCTTCGCC        3562
Ser Leu Glu Ala
            445

GTGGAGGGCG GTTTTGG                                                  3579

(2) INFORMATION FOR SEQ ID NO: 19:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO: 19:

Met Thr Pro Ala Asp Leu Ala Thr Leu Ile Lys Glu Thr Ala Val Glu
  1               5                  10                  15

Val Leu Thr Ser Arg Glu Leu Asp Thr Ser Val Leu Pro Glu Gln Val
                 20                  25                  30

Val Val Glu Arg Pro Arg Asn Pro Glu His Gly Asp Tyr Ala Thr Asn
             35                  40                  45

Ile Ala Leu Gln Val Ala Lys Lys Val Gly Gln Asn Pro Arg Asp Leu
         50                  55                  60

Ala Thr Trp Leu Ala Glu Ala Leu Ala Ala Asp Asp Ala Ile Asp Ser
```

-continued

```
                65                  70                  75                  80
        Ala Glu Ile Ala Gly Pro Gly Phe Leu Asn Ile Arg Leu Ala Ala
                        85                  90                  95

Ala Gln Gly Glu Ile Val Ala Lys Ile Leu Ala Gln Gly Glu Thr Phe
                        100                 105                 110

Gly Asn Ser Asp His Leu Ser His Leu Asp Val Asn Leu Glu Phe Val
                        115                 120                 125

Ser Ala Asn Pro Thr Gly Pro Ile His Leu Gly Gly Thr Arg Trp Ala
                        130                 135                 140

Ala Val Gly Asp Ser Leu Gly Arg Val Leu Glu Ala Ser Gly Ala Lys
        145                 150                 155                 160

Val Thr Arg Glu Tyr Tyr Phe Asn Asp His Gly Arg Gln Ile Asp Arg
                        165                 170                 175

Phe Ala Leu Ser Leu Leu Ala Ala Lys Gly Glu Pro Thr Pro Glu
                        180                 185                 190

Asp Gly Tyr Gly Gly Glu Tyr Ile Lys Glu Ile Ala Glu Ala Ile Val
                        195                 200                 205

Glu Lys His Pro Glu Ala Leu Ala Leu Glu Pro Ala Ala Thr Gln Glu
                        210                 215                 220

Leu Phe Arg Ala Glu Gly Val Glu Met Met Phe Glu His Ile Lys Ser
        225                 230                 235                 240

Ser Leu His Glu Phe Gly Thr Asp Phe Asp Val Tyr Tyr His Glu Asn
                        245                 250                 255

Ser Leu Phe Glu Ser Gly Ala Val Asp Lys Ala Val Gln Val Leu Lys
                        260                 265                 270

Asp Asn Gly Asn Leu Tyr Glu Asn Glu Gly Ala Trp Trp Leu Arg Ser
                        275                 280                 285

Thr Glu Phe Gly Asp Asp Lys Asp Arg Val Val Ile Lys Ser Asp Gly
                        290                 295                 300

Asp Ala Ala Tyr Ile Ala Gly Asp Ile Ala Tyr Val Ala Asp Lys Phe
        305                 310                 315                 320

Ser Arg Gly His Asn Leu Asn Ile Tyr Met Leu Gly Ala Asp His His
                        325                 330                 335

Gly Tyr Ile Ala Arg Leu Lys Ala Ala Ala Ala Leu Gly Tyr Lys
                        340                 345                 350

Pro Glu Gly Val Glu Val Leu Ile Gly Gln Met Val Asn Leu Leu Arg
                        355                 360                 365

Asp Gly Lys Ala Val Arg Met Ser Lys Arg Ala Gly Thr Val Val Thr
                        370                 375                 380

Leu Asp Asp Leu Val Glu Ala Ile Gly Ile Asp Ala Ala Arg Tyr Ser
        385                 390                 395                 400

Leu Ile Arg Ser Ser Val Asp Ser Ser Leu Asp Ile Asp Leu Gly Leu
                        405                 410                 415

Trp Glu Ser Gln Ser Ser Asp Asn Pro Val Tyr Tyr Val Gln Tyr Gly
                        420                 425                 430

His Ala Arg Leu Cys Ser Ile Ala Arg Lys Ala Glu Thr Leu Gly Val
                        435                 440                 445

Thr Glu Glu Gly Ala Asp Leu Ser Leu Leu Thr His Asp Arg Glu Gly
                        450                 455                 460

Asp Leu Ile Arg Thr Leu Gly Glu Phe Pro Ala Val Val Lys Ala Ala
        465                 470                 475                 480

Ala Asp Leu Arg Glu Pro His Arg Ile Ala Arg Tyr Ala Glu Glu Leu
                        485                 490                 495
```

```
Ala Gly Thr Phe His Arg Phe Tyr Asp Ser Cys His Ile Leu Pro Lys
            500                 505                 510

Val Asp Glu Asp Thr Ala Pro Ile His Thr Ala Arg Leu Ala Leu Ala
            515                 520                 525

Ala Ala Thr Arg Gln Thr Leu Ala Asn Ala Leu His Leu Val Gly Val
            530                 535                 540

Ser Ala Pro Glu Lys Met
545                 550

(2) INFORMATION FOR SEQ ID NO: 20:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO: 20:

Met Ala Thr Val Glu Asn Phe Asn Glu Leu Pro Ala His Val Trp Pro
  1                 5                  10                  15

Arg Asn Ala Val Arg Gln Glu Asp Gly Val Val Thr Val Ala Gly Val
             20                  25                  30

Pro Leu Pro Asp Leu Ala Glu Glu Tyr Gly Thr Pro Leu Phe Val Val
             35                  40                  45

Asp Glu Asp Asp Phe Arg Ser Arg Cys Arg Asp Met Ala Thr Ala Phe
         50                  55                  60

Gly Gly Pro Gly Asn Val His Tyr Ala Ser Lys Ala Phe Leu Thr Lys
 65                  70                  75                  80

Thr Ile Ala Arg Trp Val Asp Glu Glu Gly Leu Ala Leu Asp Ile Ala
                 85                  90                  95

Ser Ile Asn Glu Leu Gly Ile Ala Leu Ala Ala Gly Phe Pro Ala Ser
            100                 105                 110

Arg Ile Thr Ala His Gly Asn Asn Lys Gly Val Glu Phe Leu Arg Ala
            115                 120                 125

Leu Val Gln Asn Gly Val Gly His Val Val Leu Asp Ser Ala Gln Glu
130                 135                 140

Leu Glu Leu Leu Asp Tyr Val Ala Ala Gly Glu Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
            180                 185                 190

Gly Ser Ala Phe Glu Ala Ala Lys Ala Ala Asn Asn Ala Glu Asn Leu
            195                 200                 205

Asn Leu Val Gly Leu His Cys His Val Gly Ser Gln Val Phe Asp Ala
210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255

Gly Tyr Gly Ile Ala Tyr Thr Ala Ala Glu Glu Pro Leu Asn Val Ala
            260                 265                 270

Glu Val Ala Ser Asp Leu Leu Thr Ala Val Gly Lys Met Ala Ala Glu
            275                 280                 285

Leu Gly Ile Asp Ala Pro Thr Val Leu Val Glu Pro Gly Arg Ala Ile
            290                 295                 300
```

```
Ala Gly Pro Ser Thr Val Thr Ile Tyr Glu Val Gly Thr Thr Lys Asp
305                 310                 315                 320

Val His Val Asp Asp Asp Lys Thr Arg Arg Tyr Ile Ala Val Asp Gly
            325                 330                 335

Gly Met Ser Asp Asn Ile Arg Pro Ala Leu Tyr Gly Ser Glu Tyr Asp
            340                 345                 350

Ala Arg Val Val Ser Arg Phe Ala Glu Gly Asp Pro Val Ser Thr Arg
            355                 360                 365

Ile Val Gly Ser His Cys Glu Ser Gly Asp Ile Leu Ile Asn Asp Glu
            370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
                405                 410                 415

Arg Pro Ala Val Val Ser Val Arg Ala Gly Ser Ser Arg Leu Met Leu
            420                 425                 430

Arg Arg Glu Thr Leu Asp Asp Ile Leu Ser Leu Glu Ala
            435                 440                 445

(2) INFORMATION FOR SEQ ID NO: 21:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(iv) ANTI-SENSE: NO (xi) SEQUENCE DESCRIPTION: SEQ ID NO: 21:

CATCTAAGTA TGCATCTCGG                                              20

(2) INFORMATION FOR SEQ ID NO: 22:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(iv) ANTI-SENSE: YES (xi) SEQUENCE DESCRIPTION: SEQ ID NO: 22:

TGCCCCTCGA GCTAAATTAG                                              20

(2) INFORMATION FOR SEQ ID NO: 23:

(i) SEQUENCE CHARACTERISTICS:
        (A) LENGTH: 1034 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
         (A) ORGANISM: Brevibacterium lactofermentum
         (B) STRAIN: ATCC 13869
```

(ix) FEATURE:
    (A) NAME/KEY: CDS
    (B) LOCATION: 61..1020

(xi) SEQUENCE DESCRIPTION: SEQ ID NO: 23:

| | | | | | | |
|---|---|---|---|---|---|---|
| ATGCATCTCG GTAAGCTCGA CCAGGACAGT GCCACCACAA TTTTGGAGGA TTACAAGAAC | | | | | | 60 |

| ATG | ACC | AAC | ATC | CGC | GTA | GCT | ATC | GTG | GGC | TAC | GGA | AAC | CTG | GGA | CGC | 108 |
|---|---|---|---|---|---|---|---|---|---|---|---|---|---|---|---|---|
| Met | Thr | Asn | Ile | Arg | Val | Ala | Ile | Val | Gly | Tyr | Gly | Asn | Leu | Gly | Arg | |
| 1 | | | | 5 | | | | | 10 | | | | | 15 | | |

| AGC | GTC | GAA | AAG | CTT | ATT | GCC | AAG | CAG | CCC | GAC | ATG | GAC | CTT | GTA | GGA | 156 |
|---|---|---|---|---|---|---|---|---|---|---|---|---|---|---|---|---|
| Ser | Val | Glu | Lys | Leu | Ile | Ala | Lys | Gln | Pro | Asp | Met | Asp | Leu | Val | Gly | |
| | | | 20 | | | | | 25 | | | | | 30 | | | |

| ATC | TTC | TCG | CGC | CGG | GCC | ACC | CTC | GAC | ACA | AAG | ACG | CCA | GTC | TTT | GAT | 204 |
|---|---|---|---|---|---|---|---|---|---|---|---|---|---|---|---|---|
| Ile | Phe | Ser | Arg | Arg | Ala | Thr | Leu | Asp | Thr | Lys | Thr | Pro | Val | Phe | Asp | |
| | | 35 | | | | | 40 | | | | | 45 | | | | |

| GTC | GCC | GAC | GTG | GAC | AAG | CAC | GCC | GAC | GAC | GTG | GAC | GTG | CTG | TTC | CTG | 252 |
|---|---|---|---|---|---|---|---|---|---|---|---|---|---|---|---|---|
| Val | Ala | Asp | Val | Asp | Lys | His | Ala | Asp | Asp | Val | Asp | Val | Leu | Phe | Leu | |
| 50 | | | | | 55 | | | | | 60 | | | | | | |

| TGC | ATG | GGC | TCC | GCC | ACC | GAC | ATC | CCT | GAG | CAG | GCA | CCA | AAG | TTC | GCG | 300 |
|---|---|---|---|---|---|---|---|---|---|---|---|---|---|---|---|---|
| Cys | Met | Gly | Ser | Ala | Thr | Asp | Ile | Pro | Glu | Gln | Ala | Pro | Lys | Phe | Ala | |
| 65 | | | | | 70 | | | | | 75 | | | | | 80 | |

| CAG | TTC | GCC | TGC | ACC | GTA | GAC | ACC | TAC | GAC | AAC | CAC | CGC | GAC | ATC | CCA | 348 |
|---|---|---|---|---|---|---|---|---|---|---|---|---|---|---|---|---|
| Gln | Phe | Ala | Cys | Thr | Val | Asp | Thr | Tyr | Asp | Asn | His | Arg | Asp | Ile | Pro | |
| | | | | 85 | | | | | 90 | | | | | 95 | | |

| CGC | CAC | CGC | CAG | GTC | ATG | AAC | GAA | GCC | GCC | ACC | GCA | GCC | GGC | AAC | GTT | 396 |
|---|---|---|---|---|---|---|---|---|---|---|---|---|---|---|---|---|
| Arg | His | Arg | Gln | Val | Met | Asn | Glu | Ala | Ala | Thr | Ala | Ala | Gly | Asn | Val | |
| | | | 100 | | | | | 105 | | | | | 110 | | | |

| GCA | CTG | GTC | TCT | ACC | GGC | TGG | GAT | CCA | GGA | ATG | TTC | TCC | ATC | AAC | CGC | 444 |
|---|---|---|---|---|---|---|---|---|---|---|---|---|---|---|---|---|
| Ala | Leu | Val | Ser | Thr | Gly | Trp | Asp | Pro | Gly | Met | Phe | Ser | Ile | Asn | Arg | |
| | | 115 | | | | | 120 | | | | | 125 | | | | |

| GTC | TAC | GCA | GCG | GCA | GTC | TTA | GCC | GAG | CAC | CAG | CAG | CAC | ACC | TTC | TGG | 492 |
|---|---|---|---|---|---|---|---|---|---|---|---|---|---|---|---|---|
| Val | Tyr | Ala | Ala | Ala | Val | Leu | Ala | Glu | His | Gln | Gln | His | Thr | Phe | Trp | |
| | 130 | | | | | 135 | | | | | 140 | | | | | |

| GGC | CCA | GGT | TTG | TCA | CAG | GGC | CAC | TCC | GAT | GCT | TTG | CGA | CGC | ATC | CCT | 540 |
|---|---|---|---|---|---|---|---|---|---|---|---|---|---|---|---|---|
| Gly | Pro | Gly | Leu | Ser | Gln | Gly | His | Ser | Asp | Ala | Leu | Arg | Arg | Ile | Pro | |
| 145 | | | | | 150 | | | | | 155 | | | | | 160 | |

| GGC | GTT | CAA | AAG | GCA | GTC | CAG | TAC | ACC | CTC | CCA | TCC | GAA | GAC | GCC | CTG | 588 |
|---|---|---|---|---|---|---|---|---|---|---|---|---|---|---|---|---|
| Gly | Val | Gln | Lys | Ala | Val | Gln | Tyr | Thr | Leu | Pro | Ser | Glu | Asp | Ala | Leu | |
| | | | 165 | | | | | 170 | | | | | 175 | | | |

| GAA | AAG | GCC | CGC | CGC | GGC | GAA | GCC | GGC | GAC | CTT | ACC | GGA | AAG | CAA | ACC | 636 |
|---|---|---|---|---|---|---|---|---|---|---|---|---|---|---|---|---|
| Glu | Lys | Ala | Arg | Arg | Gly | Glu | Ala | Gly | Asp | Leu | Thr | Gly | Lys | Gln | Thr | |
| | | | 180 | | | | | 185 | | | | | 190 | | | |

| CAC | AAG | CGC | CAA | TGC | TTC | GTG | GTT | GCC | GAC | GCG | GCC | GAT | CAC | GAG | CGC | 684 |
|---|---|---|---|---|---|---|---|---|---|---|---|---|---|---|---|---|
| His | Lys | Arg | Gln | Cys | Phe | Val | Val | Ala | Asp | Ala | Ala | Asp | His | Glu | Arg | |
| | | 195 | | | | | 200 | | | | | 205 | | | | |

| ATC | GAA | AAC | GAC | ATC | CGC | ACC | ATG | CCT | GAT | TAC | TTC | GTT | GGC | TAC | GAA | 732 |
|---|---|---|---|---|---|---|---|---|---|---|---|---|---|---|---|---|
| Ile | Glu | Asn | Asp | Ile | Arg | Thr | Met | Pro | Asp | Tyr | Phe | Val | Gly | Tyr | Glu | |
| | 210 | | | | | 215 | | | | | 220 | | | | | |

| GTC | GAA | GTC | AAC | TTC | ATC | GAC | GAA | GCA | ACC | TTC | GAC | TCC | GAG | CAC | ACC | 780 |
|---|---|---|---|---|---|---|---|---|---|---|---|---|---|---|---|---|
| Val | Glu | Val | Asn | Phe | Ile | Asp | Glu | Ala | Thr | Phe | Asp | Ser | Glu | His | Thr | |
| 225 | | | | | 230 | | | | | 235 | | | | | 240 | |

| GGC | ATG | CCA | CAC | GGT | GGC | CAC | GTG | ATT | ACC | ACC | GGC | GAC | ACC | GGT | GGC | 828 |
|---|---|---|---|---|---|---|---|---|---|---|---|---|---|---|---|---|
| Gly | Met | Pro | His | Gly | Gly | His | Val | Ile | Thr | Thr | Gly | Asp | Thr | Gly | Gly | |
| | | | | 245 | | | | | 250 | | | | | 255 | | |

| TTC | AAC | CAC | ACC | GTG | GAA | TAC | ATC | CTC | AAG | CTG | GAC | CGA | AAC | CCA | GAT | 876 |
|---|---|---|---|---|---|---|---|---|---|---|---|---|---|---|---|---|
| Phe | Asn | His | Thr | Val | Glu | Tyr | Ile | Leu | Lys | Leu | Asp | Arg | Asn | Pro | Asp | |
| | | | 260 | | | | | 265 | | | | | 270 | | | |

| TTC | ACC | GCT | TCC | TCA | CAG | ATC | GCT | TTC | GGT | CGC | GCA | GCT | CAC | CGC | ATG | 924 |
|---|---|---|---|---|---|---|---|---|---|---|---|---|---|---|---|---|
| Phe | Thr | Ala | Ser | Ser | Gln | Ile | Ala | Phe | Gly | Arg | Ala | Ala | His | Arg | Met | |
| | | 275 | | | | | 280 | | | | | 285 | | | | |

```
AAG CAG CAG GGC CAA AGC GGA GCT TTC ACC GTC CTC GAA GTT GCT CCA    972
Lys Gln Gln Gly Gln Ser Gly Ala Phe Thr Val Leu Glu Val Ala Pro
    290             295                 300

TAC CTG CTC TCC CCA GAG AAC TTG GAC GAT CTG ATC GCA CGC GAC GTC   1020
Tyr Leu Leu Ser Pro Glu Asn Leu Asp Asp Leu Ile Ala Arg Asp Val
305             310                 315                 320

TAATTTAGCT CGAG                                                   1034
```

(2) INFORMATION FOR SEQ ID NO: 24:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO: 24:

```
Met Thr Asn Ile Arg Val Ala Ile Val Gly Tyr Gly Asn Leu Gly Arg
 1               5                  10                  15

Ser Val Glu Lys Leu Ile Ala Lys Gln Pro Asp Met Asp Leu Val Gly
            20                  25                  30

Ile Phe Ser Arg Arg Ala Thr Leu Asp Thr Lys Thr Pro Val Phe Asp
        35                  40                  45

Val Ala Asp Val Asp Lys His Ala Asp Asp Val Asp Val Leu Phe Leu
    50                  55                  60

Cys Met Gly Ser Ala Thr Asp Ile Pro Glu Gln Ala Pro Lys Phe Ala
65                  70                  75                  80

Gln Phe Ala Cys Thr Val Asp Thr Tyr Asp Asn His Arg Asp Ile Pro
                85                  90                  95

Arg His Arg Gln Val Met Asn Glu Ala Ala Thr Ala Ala Gly Asn Val
            100                 105                 110

Ala Leu Val Ser Thr Gly Trp Asp Pro Gly Met Phe Ser Ile Asn Arg
        115                 120                 125

Val Tyr Ala Ala Ala Val Leu Ala Glu His Gln Gln His Thr Phe Trp
    130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
                165                 170                 175

Glu Lys Ala Arg Arg Gly Glu Ala Gly Asp Leu Thr Gly Lys Gln Thr
            180                 185                 190

His Lys Arg Gln Cys Phe Val Val Ala Asp Ala Ala Asp His Glu Arg
        195                 200                 205

Ile Glu Asn Asp Ile Arg Thr Met Pro Asp Tyr Phe Val Gly Tyr Glu
    210                 215                 220

Val Glu Val Asn Phe Ile Asp Glu Ala Thr Phe Asp Ser Glu His Thr
225                 230                 235                 240

Gly Met Pro His Gly Gly His Val Ile Thr Thr Gly Asp Thr Gly Gly
                245                 250                 255

Phe Asn His Thr Val Glu Tyr Ile Leu Lys Leu Asp Arg Asn Pro Asp
            260                 265                 270

Phe Thr Ala Ser Ser Gln Ile Ala Phe Gly Arg Ala Ala His Arg Met
        275                 280                 285
```

```
Lys Gln Gln Gly Gln Ser Gly Ala Phe Thr Val Leu Glu Val Ala Pro
    290             295                 300
Tyr Leu Leu Ser Pro Glu Asn Leu Asp Asp Leu Ile Ala Arg Asp Val
305             310                 315                 320
```

METHOD OF PRODUCING L-LYSINE

This application is a continuation under 35 U.S.C. §120 of U.S. patent application Ser. No. 10/226,136, filed Aug. 23, 2002, now U.S. Pat. No. 7,846,698 which was a divisional application under 35 U.S.C. §120 of U.S. patent application Ser. No. 08/952,967, filed Dec. 8, 1997, now abandoned, which was a National Phase Patent Application under 35 U.S.C. §371 of PCT Patent App. No. PCT/JP96/01511, filed on Jun. 5, 1996, which claims priority under 35 U.S.C. §119 to Japanese Patent Application No. 7-140614, filed on Jun. 7, 1995, all of which are incorporated in their entireties by reference. A Request Under 37 U.S.C. §1.821(e) to Open New Sequence Disk File from the parent application is concurrently submitted and the sequence listing from the parent application is incorporated in its entirety.

BACKGROUND OF THE INVENTION

1. Technical Field

A method for producing L-lysine by cultivating a microorganism obtained by modifying a coryneform bacterium used for fermentative production of amino acid or the like by genetic engineering.

2. Background Art

L-Lysine, which is used as a fodder additive, is usually produced by a fermentative method by using an L-lysine-producing mutant strain belonging to the coryneform bacteria. Various L-lysine-producing bacteria known at present are those created by artificial mutation starting from wild-type strains of coryneform bacteria.

As for the coryneform bacteria, there are disclosed a vector plasmid which is autonomously replicable in bacterial cells and has a drug resistance marker gene (see U.S. Pat. No. 4,514,502), and a method for introducing a gene into bacterial cells (for example, Japanese Patent Laid-open No. 2-207791). There is also disclosed a possibility for breeding an L-threonine- or L-isoleucine-producing bacterium by using the techniques as described above (see U.S. Pat. Nos. 4,452,890 and 4,442,208). As for breeding of an L-lysine-producing bacterium, a technique is known in which a gene participating in L-lysine biosynthesis is incorporated into a vector plasmid to amplify the gene in bacterial cells (for example, Japanese Patent Laid-open No. 56-160997).

Known genes for L-lysine biosynthesis can include, for example, a dihydrodipicolinate reductase gene (Japanese Patent Laid-open No. 7-75578) and a diaminopimelate dehydrogenase gene (Ishino, S. et al., Nucleic Acids Res., 15, 3917 (1987)) in which a gene participating in L-lysine biosynthesis is cloned, as well as a phosphoenolpyruvate carboxylase gene (Japanese Patent Laid-open No. 60-87788), a dihydrodipicolinate synthase gene (Japanese Patent Publication No. 6-55149), and a diaminopimelate decarboxylase gene (Japanese Patent Laid-open No. 60-62994) in which amplification of a gene affects L-lysine productivity.

As for enzymes participating in L-lysine biosynthesis, a case is known for an enzyme which undergoes feedback inhibition when used as a wild-type. In this case, L-lysine productivity is improved by introducing an enzyme gene having such mutation that the feedback inhibition is desensitized. Those known as such a gene specifically include, for example, an aspartokinase gene (International Publication Pamphlet of WO 94/25605).

As described above, certain successful results have been obtained by means of amplification of genes for the L-lysine biosynthesis system, or introduction of mutant genes. For example, a coryneform bacterium, which harbors a mutant aspartokinase gene with desensitized concerted inhibition by lysine and threonine, produces a considerable amount of L-lysine (about 25 g/L). However, this bacterium suffers decrease in growth speed as compared with a bacterium harboring no mutant aspartokinase gene. It is also reported that L-lysine productivity is improved by further introducing a dihydrodipicolinate synthase gene in addition to a mutant aspartokinase gene (Applied and Environmental Microbiology, 57(6), 1746-1752 (1991)). However, such a bacterium suffers further decrease in growth speed.

As for the dihydrodipicolinate reductase gene, it has been demonstrated that the activity of dihydrodipicolinate reductase is increased in a coryneform bacterium into which the gene has been introduced, however, no report is included for the influence on L-lysine productivity (Japanese Patent Laid-open No. 7-75578).

In the present circumstances, no case is known for the coryneform bacteria, in which anyone has succeeded in remarkable improvement in L-lysine yield without restraining growth by combining a plurality of genes for L-lysine biosynthesis. No case has been reported in which growth is intended to be improved by enhancing a gene for L-lysine biosynthesis as well.

SUMMARY OF THE INVENTION

An aspect of the present invention is to improve the L-lysine-producing ability and the growth speed of a coryneform bacterium by using genetic materials of DNA sequences each coding for aspartokinase (hereinafter referred to as "AK", provided that a gene coding for an AK protein is hereinafter referred to as "lysC", if necessary), dihydrodipicolinate reductase (hereinafter referred to as "DDPR", provided that a gene coding for a DDPR protein is hereinafter referred to as "dapB", if necessary), dihydrodipicolinate synthase (hereinafter abbreviate as "DDPS", provided that a gene coding for a DDPS protein is hereinafter referred to as "dapA", if necessary), diaminopimelate decarboxylase (hereinafter referred to as "DDC", provided that a gene coding for a DDC protein is hereinafter referred to as "lysA", if necessary), and diaminopimelate dehydrogenase (hereinafter referred to as "DDH", provided that a gene coding for a DDH protein is hereinafter referred to as "ddh", if necessary) which are important enzymes for L-lysine biosynthesis in cells of coryneform bacteria.

When an objective substance is produced fermentatively by using a microorganism, the production speed, as well as the yield of the objective substance relative to an introduced material, is an extremely important factor. An objective substance may be produced remarkably inexpensively by increasing the production speed per a unit of fermentation equipment. Accordingly, it is industrially extremely important that the fermentative yield and the production speed are compatible with each other. The present invention proposes a solution for the problem as described above in order to fermentatively produce L-lysine by using a coryneform bacterium.

The principle of the present invention is based on the fact that the growth of a coryneform bacterium can be improved, and the L-lysine-producing speed thereof can be improved by making enhancement while combining dapB with mutant lysC (hereinafter simply referred to as "mutant lysC", if necessary) coding for mutant AK (hereinafter simply referred to as "mutant type AK", if necessary) in which concerted inhibition by lysine and threonine is desensitized, as compared with a case in which lysC is enhanced singly, and that the L-lysine-producing speed can be further improved in a stepwise manner by successively enhancing dapA, lysA, and ddh.

Namely, a recombinant DNA which is autonomously replicable in cells of coryneform bacteria is described. The recombinant DNA includes a DNA sequence coding for an aspartokinase in which feedback inhibition by L-lysine and L-threonine is substantially desensitized, and a DNA sequence coding for a dihydrodipicolinate reductase. A recombinant DNA further including a DNA sequence coding for a dihydrodipicolinate synthase is provided, in addition to each of the DNA sequences described above. A recombinant DNA further including a DNA sequence coding for a diaminopimelate decarboxylase is also provided, in addition to the three DNA sequences described above. A recombinant DNA further including a DNA sequence coding for a diaminopimelate dehydrogenase is also provided, in addition to the four DNA sequences described above.

In another aspect, the present invention provides a coryneform bacterium harboring an aspartokinase in which feedback inhibition by L-lysine and L-threonine is substantially desensitized, and comprising enhanced DNA coding for a dihydrodipicolinate reductase. The present invention provides a coryneform bacterium further comprising enhanced DNA coding for a dihydrodipicolinate synthase in the aforementioned coryneform bacterium. The present invention provides a coryneform bacterium further comprising enhanced DNA coding for a diaminopimelate decarboxylase in the aforementioned coryneform bacterium, in addition to the three DNA's described above. The present invention provides a coryneform bacterium further comprising enhanced DNA coding for a diaminopimelate dehydrogenase in the aforementioned coryneform bacterium, in addition to the four DNA's described above.

In still another aspect, the present invention provides a method for producing L-lysine comprising the steps of cultivating any one of the coryneform bacteria described above in an appropriate medium, producing and accumulating L-lysine in a culture of the bacterium, and collecting L-lysine from the culture.

The coryneform bacteria are a group of microorganisms as defined in Bergey's Manual of Determinative Bacteriology, 8th ed., p. 599 (1974), which are aerobic Gram-positive rods having no acid resistance and no spore-forming ability. The coryneform bacteria include bacteria belonging to the genus *Corynebacterium*, bacteria belonging to the genus *Brevibacterium* having been hitherto classified into the genus *Brevibacterium* but united as bacteria belonging to the genus *Corynebacterium* at present, and bacteria belonging to the genus *Brevibacterium* closely relative to bacteria belonging to the genus *Corynebacterium*.

DESCRIPTION OF PREFERRED EMBODIMENTS

Figure 1:
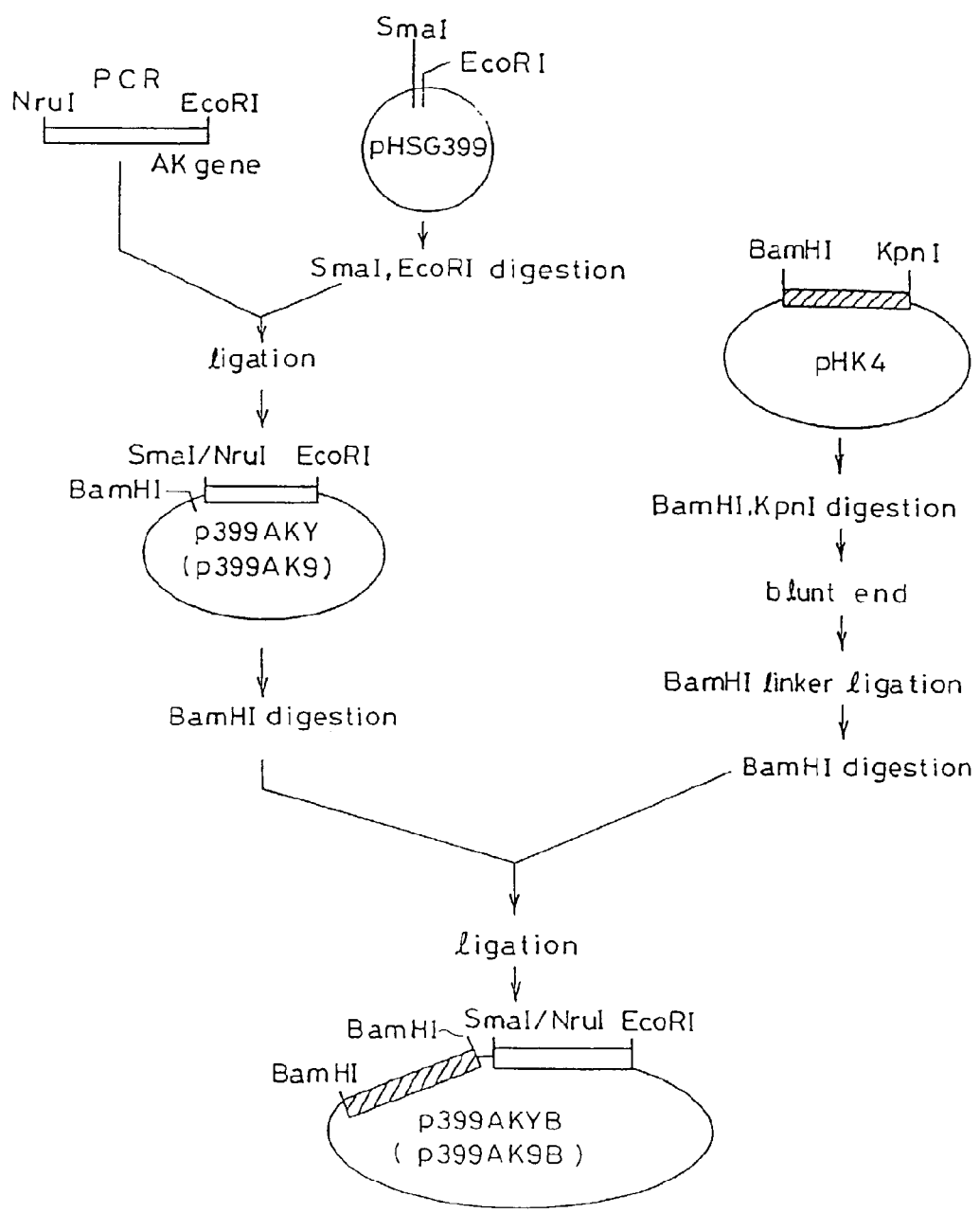
FIG. 1 illustrates a process of construction of plasmids p399AKYB and p399AK9B comprising mutant lysC.

<1> Preparation of Genes for L-lysine Biosynthesis Used for the Present Invention The genes for L-lysine biosynthesis are obtained respectively by preparing chromosomal DNA from a bacterium as a DNA donor, constructing a chromosomal DNA library by using a plasmid vector or the like, selecting a strain harboring a desired gene, and recovering, from the selected strain, recombinant DNA into which the gene has been inserted. The DNA donor for the gene for L-lysine biosynthesis is not specifically limited provided that the desired gene for L-lysine biosynthesis expresses an enzyme protein which functions in cells of coryneform bacteria. However, the DNA donor is preferably a coryneform bacterium.

All of the genes of lysC, dapA, and dapB originating from coryneform bacteria have known sequences. Accordingly, they can be obtained by performing amplification in accordance with the polymerase chain reaction method (PCR; see White, T. J. et al., Trends Genet., 5, 185 (1989)).

Each of the genes for L-lysine biosynthesis is obtainable in accordance with certain methods as exemplified below.

(1) Preparation of Mutant lysC

A DNA fragment containing mutant lysC can be prepared from a mutant strain in which synergistic feedback inhibition on the AK activity by L-lysine and L-threonine is substantially desensitized (International Publication Pamphlet of WO 94/25605). Such a mutant strain can be obtained, for example, from a group of cells originating from a wild type strain of a coryneform bacterium subjected to a mutation treatment by applying an ordinary mutation treatment such as ultraviolet irradiation and treatment with a mutating agent such as N-methyl-N'-nitro-N-nitrosoguanidine. The AK activity can be measured by using a method described by Miyajima, R. et al. in The Journal of Biochemistry (1968), 63(2), 139-148. The most preferred as such a mutant strain is represented by an L-lysine-producing bacterium AJ3445 (FERM P-1944) derived by a mutation treatment from a wild-type strain of *Brevibacterium lactofermentum* ATCC 13869 (having its changed present name of *Corynebacterium glutamicum*).

Alternatively, mutant lysC is also obtainable by an in vitro mutation treatment of plasmid DNA containing wild type lysC. In another aspect, information is specifically known on mutation to desensitize synergistic feedback inhibition on AK by L-lysine and L-threonine (International Publication Pamphlet of WO 94/25605). Accordingly, mutant lysC can be also prepared from wild type lysC on the basis of the information in accordance with, for example, the site-directed mutagenesis method.

A fragment comprising lysC can be isolated from a coryneform bacterium by preparing chromosomal DNA in accordance with, for example, a method of Saito and Miura (H. Saito and K. Miura, Biochem. Biophys. Acta, 72, 619 (1963)), and amplifying lysC in accordance with the polymerase chain reaction method (PCR; see White, T. J. et al., Trends Genet., 5, 185 (1989)).

DNA primers are exemplified by single strand DNA's of 23-mer and 21-mer having nucleotide sequences shown in SEQ ID NOs: 1 and 2 in Sequence Listing in order to amplify, for example, a region of about 1,643 bp coding for lysC based on a sequence known for *Corynebacterium glutamicum* (see Molecular Microbiology (1991), 5(5), 1197-1204; Mol. Gen. Genet. (1990), 224, 317-324). DNA can be synthesized in accordance with an ordinary method by using DNA synthesizer model 380B produced by Applied Biosystems and using the phosphoamidite method (see Tetrahedron Letters (1981), 22, 1859). PCR can be performed by using DNA Thermal Cycler Model PJ2000 produced by Takara Shuzo, and using Taq DNA polymerase in accordance with a method designated by the supplier.

lysC can be amplified by PCR and ligated with vector DNA autonomously replicable in cells of *E. coli* and/or coryneform bacteria to prepare recombinant DNA, and the recombinant DNA is introduced into cells of *E. coli* beforehand. Such provision makes following operations easy. The vector autonomously replicable in cells of *E. coli* is preferably a plasmid vector which is preferably autonomously replicable in cells of a host, including, for example, pUC19, pUC18, pBR322, pHSG299, pHSG399, pHSG398, and RSF1010.

When a DNA fragment having an ability to allow a plasmid to be autonomously replicable in coryneform bacteria is inserted into these vectors, they can be used as a so-called shuttle vector autonomously replicable in both *E. coli* and coryneform bacteria.

Such a shuttle vector includes the followings. Microorganisms harboring each of vectors and deposition numbers in international deposition facilities are shown in parentheses.

pHC4: *Escherichia coli* AJ12617 (FERM BP-3532)
pAJ655: *Escherichia coli* AJ11882 (FERM BP-136)
*Corynebacterium glutamicum* SR8201 (ATCC 39135)
pAJ1844: *Escherichia coli* AJ11883 (FERM BP-137)
*Corynebacterium glutamicum* SR8202 (ATCC 39136)
pAJ611: *Escherichia coli* AJ11884 (FERM BP-138)
pAJ3148: *Corynebacterium glutamicum* SR8203 (ATCC 39137)
pAJ440: *Bacillus subtilis* AJ11901 (FERM BP-140)

These vectors are obtainable from the deposited microorganisms as follows. Cells collected at a logarithmic growth phase were lysed by using lysozyme and SDS, followed by separation from a lysate by centrifugation at 30,000.times. g to obtain a supernatant to which polyethylene glycol is added, followed by fractionation and purification by means of cesium chloride-ethidium bromide equilibrium density gradient centrifugation.

*E. coli* can be transformed by introducing a plasmid in accordance with, for example, a method of D. M. Morrison (Methods in Enzymology, 68, 326 (1979)) or a method in which recipient cells are treated with calcium chloride to increase permeability for DNA (Mandel, M. and Higa, A., J. Mol. Biol., 53, 159 (1970)).

Wild-type lysC is obtained when lysC is isolated from an AK wild-type strain, while mutant lysC is obtained when lysC is isolated from an AK mutant strain in accordance with the method as described above.

An example of a nucleotide sequence of a DNA fragment containing wild-type lysC is shown in SEQ ID NO: 3 in Sequence Listing. An amino acid sequence of a subunit of a wild type AK protein is deduced from the nucleotide sequence, which is shown in SEQ ID NO: 4 in Sequence Listing together with the DNA sequence. Only the amino acid sequence is shown in SEQ ID NO: 5. An amino acid sequence of β-subunit of the wild type AK protein is deduced from the nucleotide sequence of DNA, which is shown in SEQ ID NO: 6 in Sequence Listing together with the DNA. Only the amino acid sequence is shown in SEQ ID NO: 7. In each of the subunits, GTG is used as an initiation codon, and a corresponding amino acid is represented by methionine. However, this representation refers to methionine, valine, or formylmethionine.

The mutant lysC is not specifically limited provided that it codes for AK in which synergistic feedback inhibition by L-lysine and L-threonine is desensitized. However, the mutant lysC is exemplified by one including mutation in which a 279th alanine residue as counted from the N-terminal is changed into an amino acid residue other than alanine and other than acidic amino acid in the α-subunit, and a 30th alanine residue is changed into an amino acid residue other than alanine and other than acidic amino acid in the β-subunit in the amino acid sequence of the wild type AK. The amino acid sequence of the wild type AK specifically includes the amino acid sequence shown in SEQ ID NO: 5 in Sequence Listing as the α-subunit, and the amino acid sequence shown in SEQ ID NO: 7 in Sequence Listing as the β-subunit.

Those preferred as the amino acid residue other than alanine and other than acidic amino acid include threonine, arginine, cyteine, phenylanaline, proline, serine, tyrosine, and valine residues.

The codon corresponding to an amino acid residue to be substituted is not specifically limited for its type provided that it codes for the amino acid residue. The amino acid sequence of the wild-type AK may slightly vary depending on the bacterial species or bacterial strain or origin. AK's, which have mutation based on, for example, substitution, deletion, or insertion of one or more amino acid residues at one or more positions irrelevant to the enzyme activity as described above, can be also used. Other AK's, which have mutation based on, for example, substitution, deletion, or insertion of other one or more amino acid residues, can be also used provided that no influence is substantially exerted on the AK activity, and on the desensitization of synergistic feedback inhibition by L-lysine and L-threonine.

An AJ12691 strain obtained by introducing a mutant lysC plasmid p399AK9B into an AJ12036 strain (FERM BP-734) as a wild-type strain of *Brevibacterium lactofermentum* has been deposited on Apr. 10, 1992 under the deposit number of FERM P-12918 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan), and then converted to a international deposit based on the Budapest Treaty on Feb. 10, 1995, and given deposit number of FERM BP-4999.

(2) Preparation of dapB

A DNA fragment containing dapB can be prepared from chromosome of a coryneform bacterium by means of PCR. The DNA donor is not specifically limited, however, it can be exemplified by *Brevibacterium lactofermentum* ATCC 13869 strain.

A DNA sequence coding for DDPR is known for *Brevibacterium lactofermentum* (Journal of Bacteriology, 175(9), 2743-2749 (1993)), on the basis of which DNA primers for PCR can be prepared. Such DNA primers are specifically exemplified by DNA's of 23-mers respectively having nucleotide sequences depicted in SEQ ID NOs: 8 and 9 in Sequence Listing. Synthesis of DNA, PCR, and preparation of a plasmid containing obtained dapB can be performed in the same manner as those for lysC described above.

A nucleotide sequence of a DNA fragment containing dapB and an amino acid sequence deduced from the nucleotide sequence are illustrated in SEQ ID NO: 10. Only the amino acid sequence is shown in SEQ ID NO: 11. In addition to DNA fragments coding for this amino acid sequence, the present invention can equivalently use DNA fragments coding for amino acid sequences substantially the same as the amino acid sequence shown in SEQ ID NO: 11, namely amino acid sequences having mutation based on, for example, substitution, deletion, or insertion of one or more amino acids provided that there is no substantial influence on the DDPR activity.

A transformant strain AJ13107 obtained by introducing a plasmid PCRDAPB containing dapB obtained in Example described later on into *E. coli* JM109 strain was internationally deposited on May 26, 1995 under a deposition number of FERM BP-5114 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan) based on the Budapest Treaty.

(3) Preparation of dapA

A DNA fragment containing dapA can be prepared from chromosome of a coryneform bacterium by means of PCR. The DNA donor is not specifically limited, however, it can be exemplified by *Brevibacterium lactofermentum* ATCC 13869 strain.

A DNA sequence coding for DDPS is known for *Corynebacterium glutamicum* (see Nucleic Acids Research, 18(21), 6421 (1990); EMBL accession No. X53993), on the basis of which DNA primers for PCR can be prepared. Such DNA primers are specifically exemplified by DNA's of 23-mers respectively having nucleotide sequences depicted in SEQ ID NOs: 12 and 13 in Sequence Listing. Synthesis of DNA, PCR, and preparation of a plasmid containing obtained dapA can be performed in the same manner as those for lysC described above.

A nucleotide sequence of a DNA fragment containing dapA and an amino acid sequence deduced from the nucleotide sequence are exemplified in SEQ ID NO: 14. Only the amino acid sequence is shown in SEQ ID NO: 15. In addition to DNA fragments coding for this amino acid sequence, the present invention can equivalently use DNA fragments coding for amino acid sequences substantially the same as the amino acid sequence shown in SEQ ID NO: 15, namely amino acid sequences having mutation based on, for example, substitution, deletion, or insertion of one or more amino acids provided that there is no substantial influence on the DDPS activity.

A transformant strain AJ13106 obtained by introducing a plasmid pCRDAPA containing dapA obtained in Example described later on into *E. coli* JM109 strain was internationally deposited on May 26, 1995 under a deposition number of FERM BP-5113 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan) based on the Budapest Treaty.

(4) Preparation of lysA

A DNA fragment containing lysA can be prepared from chromosome of a coryneform bacterium by means of PCR. The DNA donor is not specifically limited, however, it is exemplified by *Brevibacterium lactofermentum* ATCC 13869 strain.

In the coryneform bacteria, lysA forms an operon together with argS (arginyl-tRNA synthase gene), and lysA exists downstream from argS. Expression of lysA is regulated by a promoter existing upstream from argS (see Journal of Bacteriology, November, 7356-7362 (1993)). DNA sequences of these genes are known for *Corynebacterium glutamicum* (see Molecular Microbiology, 4(11), 1819-1830 (1990); Molecular and General Genetics, 212, 112-119 (1988)), on the basis of which DNA primers for PCR can be prepared. Such DNA primers are specifically exemplified by DNA's of 23-mers respectively having nucleotide sequences shown in SEQ ID NO: 16 in Sequence Listing (corresponding to nucleotide numbers 11 to 33 in a nucleotide sequence described in Molecular Microbiology, 4(11), 1819-1830 (1990)) and SEQ ID NO: 17 (corresponding to nucleotide numbers 1370 to 1392 in a nucleotide sequence described in Molecular and General Genetics, 212, 112-119 (1988)). Synthesis of DNA, PCR, and preparation of a plasmid containing obtained lysA can be performed in the same manner as those for lysC described above.

In Example described later on, a DNA fragment containing a promoter, argS, and lysA was used in order to enhance lysA. However, argS is not essential. A DNA fragment in which lysA is ligated just downstream from a promoter can be used.

A nucleotide sequence of a DNA fragment containing argS and lysA, and an amino acid sequence deduced to be encoded by the nucleotide sequence are exemplified in SEQ ID NO: 18. An example of an amino acid sequence encoded by argS is shown in SEQ ID NO: 19, and an example of an amino acid sequence encoded by lysA is shown in SEQ ID NO: 20. In addition to DNA fragments coding for these amino acid sequences, DNA fragments coding for amino acid sequences substantially the same as the amino acid sequence shown in SEQ ID NO: 20 can be used, namely amino acid sequences having mutation based on, for example, substitution, deletion, or insertion of one or more amino acids provided that there is no substantial influence on the DDC activity.

(5) Preparation of ddh

A DNA fragment containing ddh can be prepared from chromosome of a coryneform bacterium by means of PCR. The DNA donor is not specifically limited, however, it can be exemplified by *Brevibacterium lactofermentum* ATCC 13869 strain.

A DDH gene is known for *Corynebacterium glutamicum* (Ishino, S. et al., Nucleic Acids Res., 15, 3917 (1987)), on the basis of which primers for PCR can be prepared. Such DNA primers are specifically exemplified by DNA's of 20-mers respectively having nucleotide sequences depicted in SEQ ID NOs: 21 and 22 in Sequence Listing. Synthesis of DNA, PCR, and preparation of a plasmid containing obtained ddh can be performed in the same manner as those for lysC described above.

A nucleotide sequence of a DNA fragment containing ddh and an amino acid sequence deduced from the nucleotide sequence are illustrated in SEQ ID NO: 23. Only the amino acid sequence is shown in SEQ ID NO: 24. In addition to DNA fragments coding for this amino acid sequence, DNA fragments coding for amino acid sequences substantially the same as the amino acid sequence shown in SEQ ID NO: 24 can be used, namely amino acid sequences having mutation based on, for example, substitution, deletion, or insertion of one or more amino acids provided that there is no substantial influence on the DDH activity.

<2> Recombinant DNA and Coryneform Bacterium of the Present Invention

The coryneform bacterium can contain an aspartokinase (mutant AK) in which feedback inhibition by L-lysine and L-threonine is substantially desensitized, wherein DNA (dapB) coding for a dihydrodipicolinate reductase is enhanced. In one example, the coryneform bacterium contains a DNA (dapA) coding for dihydrodipicolinate synthase which is further enhanced. In another example, the coryneform bacterium contains a DNA (lysA) coding for diaminopimelate decarboxylase which is further enhanced. In another example, the coryneform bacterium contains a DNA (ddh) coding for diaminopimelate dehydrogenase which is further enhanced.

The term "enhance" can refer to the fact that the intracellular activity of an enzyme encoded by the DNA is raised by, for example, increasing the copy number of a gene, using a strong promoter, using a gene coding for an enzyme having a high specific activity, or combining these means.

The coryneform bacterium harboring the mutant AK may be those which produce the mutant aspartokinase as a result of mutation, or those which are transformed by introducing mutant lysC.

Examples of the coryneform bacterium used to introduce the DNA described above include, for example, the following lysine-producing wild-type strains:

Corynebacterium acetoacidophilum ATCC 13870;
Corynebacterium acetoglutamicum ATCC 15806;
Corynebacterium callunae ATCC 15991;
Corynebacterium glutamicum ATCC 13032;
(Brevibacterium divaricatum) ATCC 14020;
(Brevibacterium lactofermentum) ATCC 13869;
(Corynebacterium lilium) ATCC 15990;
(Brevibacterium flavum) ATCC 14067;
Corynebacterium melassecola ATCC 17965;
Brevibacterium saccharolyticum ATCC 14066;
Brevibacterium immariophilum ATCC 14068;
Brevibacterium roseum ATCC 13825;
Brevibacterium thiogenitalis ATCC 19240;
Microbacterium ammoniaphilum ATCC 15354;
Corynebacterium thermoaminoqenes AJ12340 (FERM BP-1539).

Other than the bacterial strains described above, those usable as a host include, for example, mutant strains having an L-lysine-producing ability derived from the aforementioned strains. Such artificial mutant strains includes the followings: S-(2-aminoethyl)-cysteine (hereinafter abbreviated as "AEC") resistant mutant strains (Brevibacterium lactofermentum AJ11082 (NRRL B-1147), Japanese Patent Publication Nos. 56-1914, 56-1915, 57-14157, 57-14158, 57-30474, 58-10075, 59-4993, 61-35840, 62-24074, 62-36673, 5-11958, 7-112437, and 7-112438); mutant strains which require amino acid such as L-homoserine for their growth (Japanese Patent Publication Nos. 48-28078 and 56-6499); mutant strains which exhibit resistance to AEC and require amino acids such as L-leucine, L-homoserine, L-proline, L-serine, L-arginine, L-alanine, and L-valine (U.S. Pat. Nos. 3,708,395 and 3,825,472); L-lysine-producing mutant strains which exhibit resistance to DL-α-amino-ε-cap-rolactam, α-amino-lauryllactam, aspartate-analog, sulfa drug, quinoid, and N-lauroylleucine; L-lysine-producing mutant strains which exhibit resistance to inhibitors of oxyaloacetate decarboxylase or respiratory system enzymes (Japanese Patent Laid-open Nos. 50-53588, 50-31093, 52-102498, 53-9394, 53-86089, 55-9783, 55-9759, 56-32995 and 56-39778, and Japanese Patent Publication Nos. 53-43591 and 53-1833); L-lysine-producing mutant strains which require inositol or acetic acid (Japanese Patent Laid-open Nos. 55-9784 and 56-8692); L-lysine-producing mutant strains which exhibit sensitivity to fluoropyruvic acid or temperature not less than 34.degree. C. (Japanese Patent Laid-open Nos. 55-9783 and 53-86090); and producing mutant strains belonging to the genus Brevibacterium or Corynebacterium which exhibit resistance to ethylene glycol and produce L-lysine (U.S. Pat. No. 4,411,997).

In a specified example, in order to enhance the genes for L-lysine biosynthesis in the host as described above, the genes are introduced into the host by using a plasmid vector, transposon or phage vector or the like. Upon the introduction, it is expected to make enhancement to some extent even by using a low copy type vector. However, multiple copy type vector can also be used. Such a vector includes, for example, plasmid vectors, pAJ655, pAJ1844, pAJ611, pAJ3148, and pAJ440 described above. Besides, transposons derived from coryneform bacteria are described in International Publication Pamphlets of WO02/02627 and WO93/18151, European Patent Publication No. 445385, Japanese Patent Laid-open No. 6-46867, Vertes, A. A. et al., Mol. Microbiol., 11, 739-746 (1994), Bonamy, C., et al., Mol. Microbiol., 14, 571-581 (1994), Vertes, A. A. et al., Mol. Gen. Genet., 245, 397-405 (1994), Jagar, W. et al., FEMS Microbiology Letters, 126, 1-6 (1995), Japanese Patent Laid-open No. 7-107976, Japanese Patent Laid-open No. 7-327680 and the like.

The mutant lysC is not necessarily enhanced. It is allowable to use those which have mutation on lysC on chromosomal DNA, or in which the mutant lysC is incorporated into chromosomal DNA. Alternatively, the mutant lysC may be introduced by using a plasmid vector. On the other hand, dapA, dapB, lysA, and ddh can be enhanced in order to efficiently produce L-lysine.

Each of the genes of lysC, dapA, dapB, lysA, and ddh may be successively introduced into the host by using different vectors respectively. Alternatively, two, three, four, or five species of the genes may be introduced together by using a single vector. When different vectors are used, the genes may be introduced in any order, however, it is preferred to use vectors which have a stable sharing and harboring mechanism in the host, and which are capable of co-existing with each other.

A coryneform bacterium harboring the mutant AK and further including enhanced dapB is obtained, for example, by introducing, into a host coryneform bacterium, a recombinant DNA containing mutant lysC and dapB autonomously replicable in cells of coryneform bacteria.

A coryneform bacterium further including enhanced dapA in addition to mutant lysC and dapB is obtained, for example, by introducing, into a host coryneform bacterium, a recombinant DNA containing mutant lysC, dapB, and dapA autonomously replicable in cells of coryneform bacteria.

A coryneform bacterium further including enhanced lysA in addition to mutant lysC, dapB, and dapA is obtained, for example, by introducing, into a host coryneform bacterium, a recombinant DNA containing mutant lysC, dapB, dapA, and lysA autonomously replicable in cells of coryneform bacteria.

A coryneform bacterium further including enhanced ddh in addition to mutant lysC, dapB, dapA, and lysA is obtained, for example, by introducing, into a host coryneform bacterium, a recombinant DNA containing mutant lysC, dapB, dapA, lysA, and ddh autonomously replicable in cells of coryneform bacteria.

The above-mentioned recombinant DNAs can be obtained, for example, by inserting each of the genes participating in L-lysine biosynthesis into a vector such as plasmid vector, transposon or phage vector as described above.

In the case in which a plasmid is used as a vector, the recombinant DNA can be introduced into the host in accordance with an electric pulse method (Sugimoto et al., Japanese Patent Laid-open No. 2-207791). Amplification of a gene using transposon can be performed by introducing a plasmid which carrying a transposon into the host cell and inducing transposition of the transposon.

<3> Method for Producing L-lysine

L-Lysine can be efficiently produced by cultivating, in an appropriate medium, the coryneform bacterium containing the enhanced genes for L-lysine biosynthesis as described above, producing and accumulating L-lysine in a culture of the bacterium, and collecting L-lysine from the culture.

The medium can be exemplified by an ordinary medium containing a carbon source, a nitrogen source, inorganic ions, and optionally other organic components.

As the carbon source, it is possible to use sugars such as glucose, fructose, sucrose, molasses, and starch hydrolysate; and organic acids such as fumaric acid, citric acid, and succinic acid.

As the nitrogen source, it is possible to use inorganic ammonium salts such as ammonium sulfate, ammonium chloride, and ammonium phosphate; organic nitrogen such as soybean hydrolysate; ammonia gas; and aqueous ammonia.

As organic trace nutrient sources, it is possible that required substances such as vitamin $B_1$ and L-homoserine or yeast extract or the like in appropriate amounts can be used. Other than the above, potassium phosphate, magnesium sulfate, iron ion, manganese ion and so on can be added in small amounts, if necessary.

Cultivation can be carried out under an aerobic condition for about 30 to 90 hours. The cultivation temperature can be controlled at 25.degree. C. to 37.degree. C., and pH can be controlled at 5 to 8 during cultivation. Inorganic or organic, acidic or alkaline substances, or ammonia gas or the like can be used for pH adjustment. L-lysine can be collected from a culture by combining an ordinary ion exchange resin method, a precipitation method, and other known methods.

EXAMPLES

The present invention will be more specifically explained below with reference to the following non-limiting Examples.

Example 1

Preparation of Wild Type lysC Gene and Mutant lysC Gene from *Brevibacterium lactofermentum* \

<1> Preparation of Wild Type and Mutant lysC's and Preparation of Plasmids Containing them A strain of *Brevibacterium lactofermentum* ATCC 13869, and an L-lysine-producing mutant strain AJ3445 (FERM P-1944) obtained from the ATCC 13869 strain by a mutation treatment were used as chromosomal DNA donors. The AJ3445 strain had been subjected to mutation so that lysC was changed to involve substantial desensitization from concerted inhibition by lysine and threonine (Journal of Biochemistry, 68, 701-710 (1970)).

A DNA fragment containing lysC was amplified from chromosomal DNA in accordance with the PCR method (polymerase chain reaction; see White, T. J. et al., Trends Genet., 5, 185 (1989)). As for DNA primers used for amplification, single strand DNA's of 23-mer and 21-mer having nucleotide sequences shown in SEQ ID NOs: 1 and 2 were synthesized in order to amplify a region of about 1,643 bp coding for lysC on the basis of a sequence known for *Corynebacterium glutamicum* (see Molecular Microbiology (1991), 5(5), 1197-1204; and Mol. Gen. Genet. (1990), 224, 317-324). DNA was synthesized in accordance with an ordinary method by using DNA synthesizer model 380B produced by Applied Biosystems and using the phosphoamidite method (see Tetrahedron Letters (1981), 22, 1859).

The gene was amplified by PCR by using DNA Thermal Cycler Model PJ2000 produced by Takara Shuzo, and using Taq DNA polymerase in accordance with a method designated by the supplier. An amplified gene fragment of 1,643 kb was confirmed by agarose gel electrophoresis. After that, the fragment excised from the gel was purified in accordance with an ordinary method, and it was digested with restriction enzymes NruI (produced by Takara Shuzo) and EcoRI (produced by Takara Shuzo). pHSG399 (see Takeshita, S. et al., Gene (1987), 61, 63-74) was used as a cloning vector for the gene fragment. pHSG399 was digested with restriction enzymes SmaI (produced by Takara Shuzo) and EcoRI, and it was ligated with the amplified lysC fragment. DNA was ligated by using DNA ligation kit (produced by Takara Shuzo) in accordance with a designated method. Thus plasmids were prepared, in which the lysC fragments amplified from chromosomes of *Brevibacterium lactofermentum* were ligated with pHSG399 respectively. A plasmid comprising lysC from ATCC 13869 (wild type strain) was designated as p399AKY, and a plasmid comprising lysC from AJ3463 (L-lysine-producing bacterium) was designated as p399AK9.

A DNA fragment (hereinafter referred to as "Brevi.-ori") having an ability to make a plasmid autonomously replicable in bacteria belonging to the genus *Corynebacterium* was introduced into p399AKY and p399AK9 respectively to prepare plasmids carrying lysC autonomously replicable in bacteria belonging to the genus *Corynebacterium*. Brevi.-ori was prepared from a plasmid vector pHK4 containing Brevi.-ori and autonomously replicable in cells of both *Escherichia coli* and bacteria belonging to the genus *Corynebacterium*. pHK4 was constructed by digesting pHC4 with KpnI (produced by Takara Shuzo) and BamHI (produced by Takara Shuzo), extracting a Brevi.-ori fragment, and ligating it with pHSG298 having been also digested with KpnI and BamHI (see Japanese Patent Laid-open No. 5-7491). pHK4 gives kanamycin resistance to a host. *Escherichia coli* harboring pHK4 was designated as *Escherichia coli* AJ13136, and deposited on Aug. 1, 1995 under a deposition number of FERM BP-5186 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan).

pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKY and p399AK9 having been also digested with BamHI respectively to prepare plasmids each containing the lysC gene autonomously replicable in bacteria belonging to the genus Corynebacterium.

A plasmid containing the wild type lysC gene originating from p399AKY was designated as p399AKYB, and a plasmid containing the mutant lysC gene originating from p399AK9 was designated as p399AK9B. The process of construction of p399AK9B and p399AKYB is shown in FIG. 1. A strain AJ12691 obtained by introducing the mutant lysC plasmid p399AK9B into a wild type strain of Brevibacterium lactofermentum (AJ12036 strain, FERM BP-734) was deposited on Apr. 10, 1992 under a deposition number of FERM P-12918 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan), and converted to international deposition based on the Budapest Treaty on Feb. 10, 1995, and deposited under a deposition number of FERM BP-4999.

<2> Determination of Nucleotide Sequences of Wild Type lysC and Mutant lysC from Brevibacterium lactofermentum The plasmid p399AKY containing the wild type lysC and the plasmid p399AK9 containing the mutant lysC were prepared from the respective transformants to determine nucleotide sequences of the wild type and mutant lysC's. Nucleotide sequence determination was performed in accordance with a method of Sanger et al. (for example, F. Sanger et al., Proc. Natl. Acad. Sci., 74, 5463 (1977)).

The nucleotide sequence of wild type lysC encoded by p399AKY is shown in SEQ ID NO: 3 in Sequence Listing. On the other hand, the nucleotide sequence of mutant lysC encoded by p399AK9 had only mutation of one nucleotide such that 1051th G was changed into A in SEQ ID NO: 3 as compared with wild type lysC. It is known that lysC of Corynebacterium glutamicum has two subunits ($\alpha$, $\beta$) encoded in an identical reading frame on an identical DNA strand (see Kalinowski, J. et al., Molecular Microbiology (1991) 5(5), 1197-1204). Judging from homology, it is assumed that the gene sequenced herein also has two subunits ($\alpha$, $\beta$) encoded in an identical reading frame on an identical DNA strand.

An amino acid sequence of the $\beta$-subunit of the wild type AK protein deduced from the nucleotide sequence of DNA is shown in SEQ ID NO: 4 together with the DNA sequence. Only the amino acid sequence is shown in SEQ ID NO: 5. An amino acid sequence of the $\beta$-subunit of the wild type AK protein deduced from the nucleotide sequence of DNA is shown in SEQ ID NO: 6 together with DNA. Only the amino acid sequence is shown in SEQ ID NO: 7. In each of the subunits, GTG is used as an initiation codon, and a corresponding amino acid is represented by methionine. However, this representation refers to methionine, valine, or formylmethionine.

On the other hand, mutation on the sequence of mutant lysC means occurrence of amino acid residue substitution such that a 279th alanine residue of the $\alpha$-subunit is changed into a threonine residue, and a 30th alanine residue of the $\beta$-subunit is changed into a threonine residue in the amino acid sequence of the wild type AK protein (SEQ ID NOs: 5, 7).

Example 2

Preparation of dapB from Brevibacterium lactofermentum

<1> Preparation of dapB and Construction of Plasmid Containing dapB

A wild type strain of Brevibacterium lactofermentum ATCC 13869 was used as a chromosomal DNA donor. Chromosomal DNA was prepared from the ATCC 13869 strain in accordance with an ordinary method. A DNA fragment containing dapB was amplified from the chromosomal DNA in accordance with PCR. As for DNA primers used for amplification, DNA's of 23-mers having nucleotide sequences depicted in SEQ ID NOs: 8 and 9 in Sequence Listing respectively were synthesized in order to amplify a region of about 2.0 kb coding for DDPR on the basis of a sequence known for Brevibacterium lactofermentum (see Journal of Bacteriology, 157(9), 2743-2749 (1993)). Synthesis of DNA and PCR were performed in the same manner as described in Example 1. pCR-Script (produced by Invitrogen) was used as a cloning vector for the amplified gene fragment of 2,001 bp, which was ligated with the amplified dapB fragment. Thus a plasmid was constructed, in which the dapB fragment of 2,001 bp amplified from chromosome of Brevibacterium lactofermentum was ligated with pCR-Script. The plasmid obtained as described above, which had dapB originating from ATCC 13869, was designated as pCRDAPB. A transformant strain AJ13107 obtained by introducing pCRDAPB into E. coli JM109 strain has been internationally deposited since May 26, 1995 under a deposition number of FERM BP-5114 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan) based on the Budapest Treaty.

A fragment of 1,101 bp containing a structural gene of DDPR was extracted by digesting pCRDAPB with EcoRV and SphI. This fragment was ligated with pHSG399 having been digested with HincII and SphI to prepare a plasmid. The prepared plasmid was designated as p399DPR.

Figure 2:
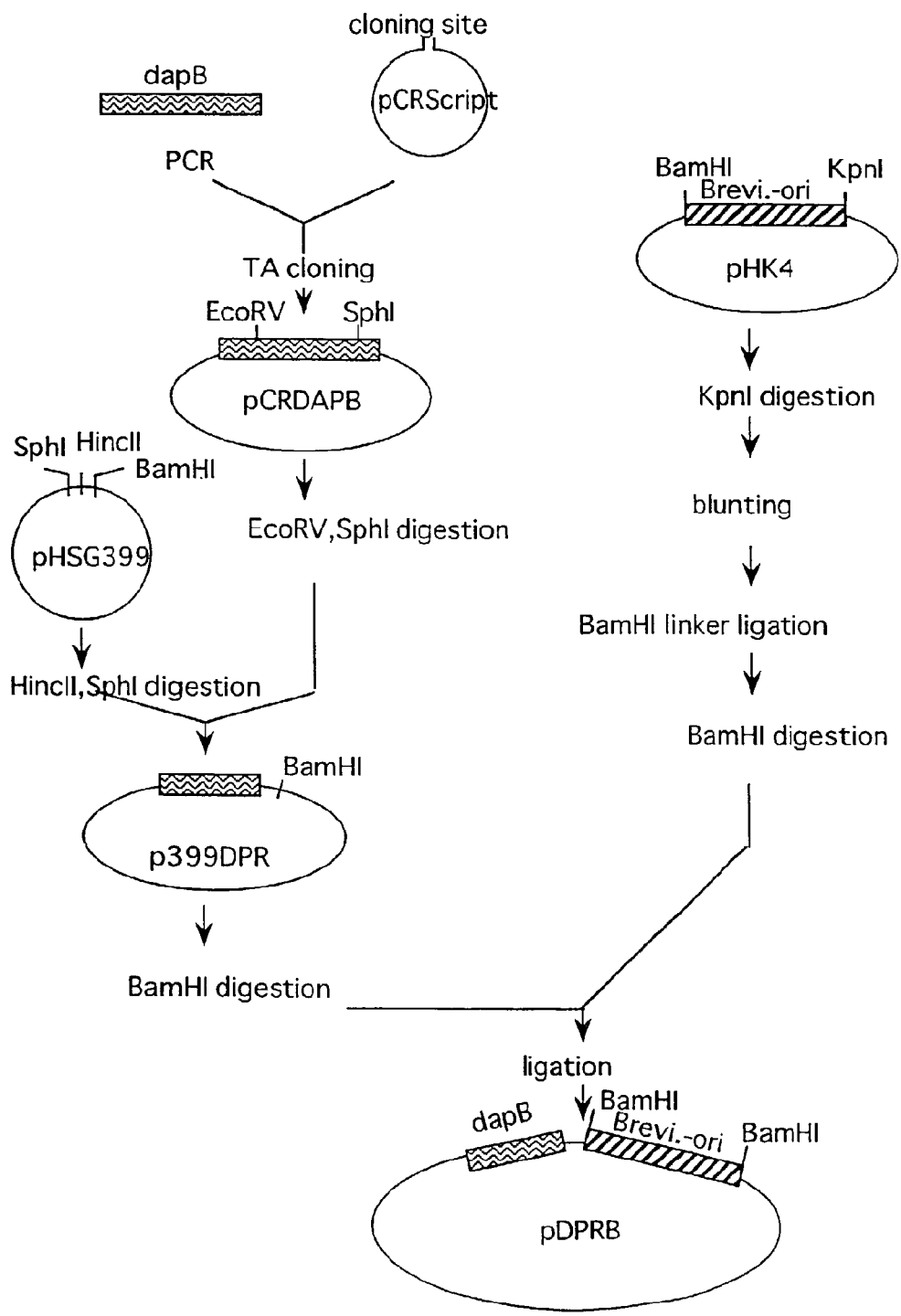
FIG. 2 illustrates a process of construction of a plasmid pDPRB comprising dapB and Brevi.-ori.

Brevi.-ori was introduced into the prepared p399DPR to construct a plasmid carrying dapB autonomously replicable in coryneform bacteria. pHK4 was digested with a restriction enzyme KpnI (produced by Takara Shuzo), and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399DPR having been also digested with BamHI to prepare a plasmid containing dapB autonomously replicable in coryneform bacteria. The prepared plasmid was designated as pDPRB. The process of construction of pDPRB is shown in FIG. 2.

<2> Determination of Nucleotide Sequence of dapB from Brevibacterium lactofermentum Plasmid DNA was prepared from the AJ13107 strain harboring p399DPR, and its nucleotide sequence was determined in the same manner as described in Example 1. A determined nucleotide sequence and an amino acid sequence deduced from the nucleotide sequence are shown in SEQ ID NO: 10. Only the amino acid sequence is shown in SEQ ID NO: 11.

Example 3

Preparation of dapA from *Brevibacterium lactofermentum*

<1> Preparation of dapA and Construction of Plasmid Containing dapA

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing dapA was amplified from the chromosomal DNA in accordance with PCR. As for DNA primers used for amplification, DNA's of 20-mers having nucleotide sequences shown in SEQ ID NOs: 12 and 13 in Sequence Listing respectively were synthesized in order to amplify a region of about 1.5 kb coding for DDPS on the basis of a sequence known for *Corynebacterium glutamicum* (see Nucleic Acids Research, 18(21), 6421 (1990); EMBL accession No. X53993). Synthesis of DNA and PCR were performed in the same manner as described in Example 1. pCR1000 (produced by Invitrogen, see Bio/Technology, 9, 657-663 (1991)) was used as a cloning vector for the amplified gene fragment of 1,411 bp, which was ligated with the amplified dapA fragment. Ligation of DNA was performed by using DNA ligation kit (produced by Takara Shuzo) in accordance with-a designated method. Thus a plasmid was constructed, in which the dapA fragment of 1,411 bp amplified from chromosome of *Brevibacterium lactofermentum* was ligated with pCR1000. The plasmid obtained as described above, which had dapA originating from ATCC 13869, was designated as PCRDAPA.

A transformant strain AJ13106 obtained by introducing pCRDAPA into *E. coli* JM109 strain has been internationally deposited since May 26, 1995 under a deposition number of FERM BP-5113 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan) based on the Budapest Treaty.

Figure 3:
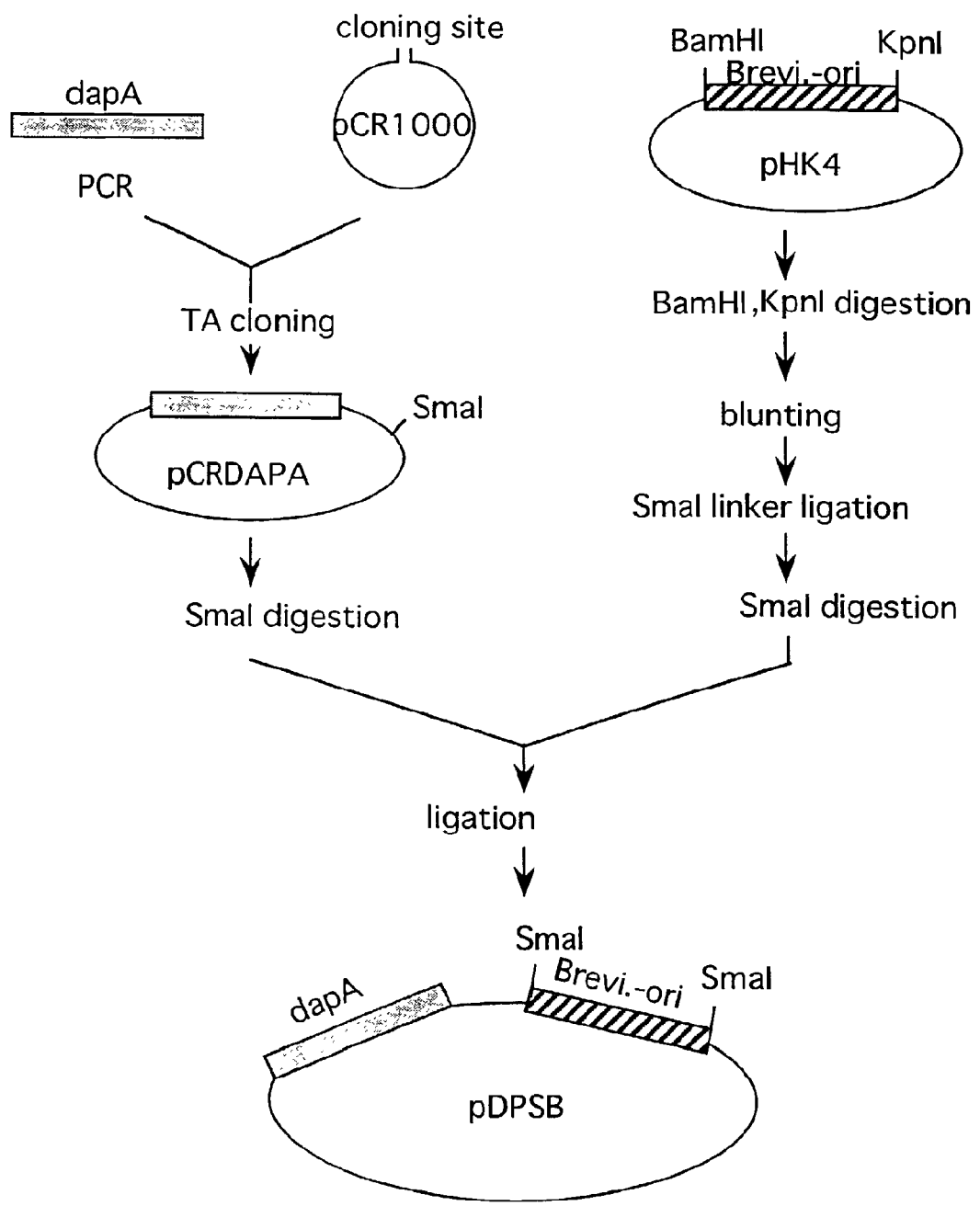
FIG. 3 illustrates a process of construction of a plasmid PDPSB comprising dapA and Brevi.-ori.

Brevi.-ori was introduced into the prepared pCRDAPA to construct a plasmid carrying dapA autonomously replicable in coryneform bacteria. pHK4 was digested with restriction enzymes KpnI and BamHI (produced by Takara Shuzo), and cleaved edges were blunt-ended. Blunt end formation was performed by using DNA Blunting kit (produced by Takara Shuzo) in accordance with a designated method. After the blunt end formation, a phosphorylated SmaI linker (produced by Takara Shuzo) was ligated to make modification so that the DNA fragment corresponding to the Brevi.-ori portion might be excised from pHK4 by digestion with only SmaI. This plasmid was digested with SmaI, and the generated Brevi.-ori DNA fragment was ligated with pCRDAPA having been also digested with SmaI to prepare a plasmid containing dapA autonomously replicable in coryneform bacteria. This plasmid was designated as pDPSB. The process of construction of pDPSB (Km.sup.r) is shown in FIG. 3.

<2> Determination of Nucleotide Sequence of dapA from *Brevibacterium lactofermentum*

Plasmid DNA was prepared from the AJ13106 strain harboring pCRDAPA, and its nucleotide sequence was determined in the same manner as described in Example 1. A determined nucleotide sequence and an amino acid sequence deduced from the nucleotide sequence are shown in SEQ ID NO: 14. Only the amino acid sequence is shown in SEQ ID NO: 15.

Example 4

Preparation of lysA from *Brevibacterium lactofermentum*

<1> Preparation of lysA and Construction of Plasmid Containing lysA

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing argS, lysA, and a promoter of an operon containing them was amplified from the chromosomal DNA in accordance with PCR. As for DNA primers used for amplification, synthetic DNA's of 23-mers having nucleotide sequences depicted in SEQ ID NOs: 16 and 17 in Sequence Listing respectively were used in order to amplify a region of about 3.6 kb coding for arginyl-tRNA synthase and DDC on the basis of a sequence known for *Corynebacterium glutamicum* (see Molecular Microbiology, 4(11), 1819-1830 (1990); Molecular and General Genetics, 212, 112-119 (1988)). Synthesis of DNA and PCR were performed in the same manner as described in Example 1. pHSG399 was used as a cloning vector for the amplified gene fragment of 3,579 bp. pHSG399 was digested with a restriction enzyme SmaI (produced by Takara Shuzo), which was ligated with the DNA fragment containing amplified lysA. A plasmid obtained as described above, which had lysA originating from ATCC 13869, was designated as p399LYSA.

Figure 4:
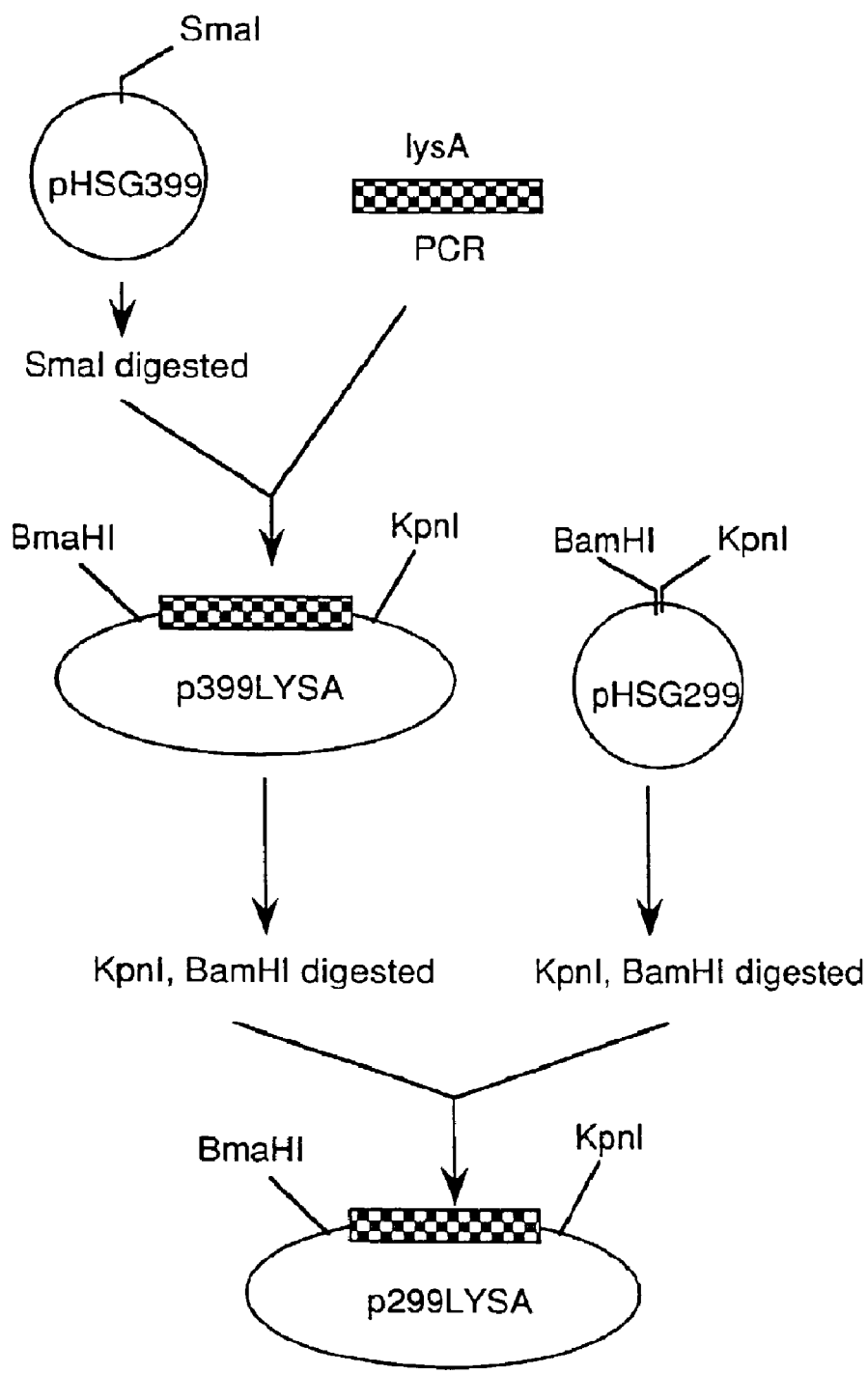
FIG. 4 illustrates a process of construction of a plasmid p299LYSA comprising lysA.

A DNA fragment containing lysA was extracted by digesting p399LYSA with KpnI (produced by Takara Shuzo) and BamHI (produced by Takara Shuzo). This DNA fragment was ligated with pHSG299 having been digested with KpnI and BamHI. An obtained plasmid was designated as p299LYSA. The process of construction of p299LYSA is shown in FIG. 4.

Figure 5:
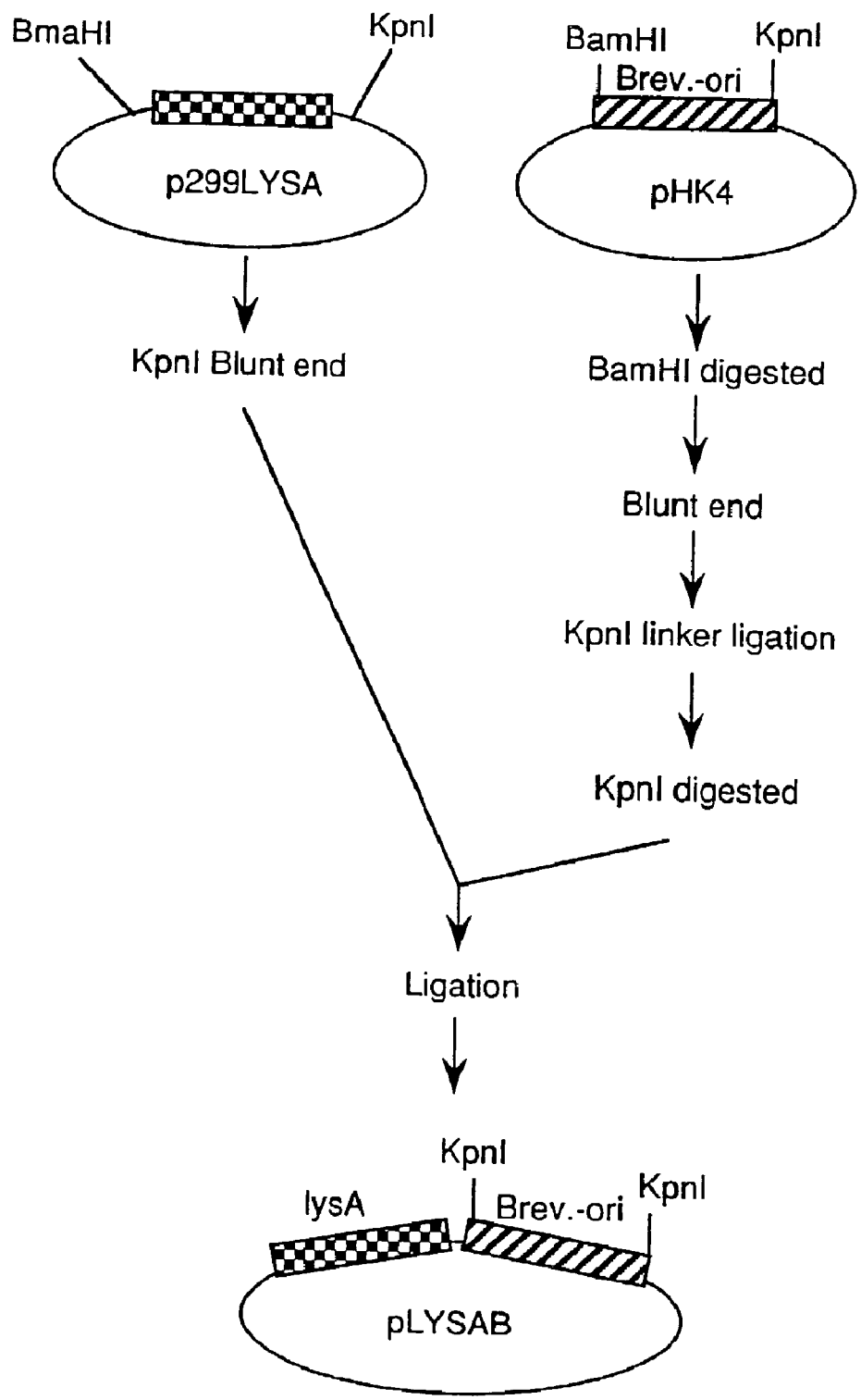
FIG. 5 illustrates a process of construction of a plasmid pLYSAB comprising lysA and Brevi.-ori.

Brevi.-ori was introduced into the obtained p299LYSA to construct a plasmid carrying lysA autonomously replicable in coryneform bacteria. pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p299LYSA having been also digested with KnI to prepare a plasmid containing lysA autonomously replicable in coryneform bacteria. The prepared plasmid was designated as pLYSAB. The process of construction of pLYSAB is shown in FIG. 5.

<2> Determination of Nucleotide Sequence of lysA from *Brevibacterium lactofermentum*

Plasmid DNA of p299LYSA was prepared, and its nucleotide sequence was determined in the same manner as described in Example 1. A determined nucleotide sequence and an amino acid sequence deduced to be encoded by the nucleotide sequence are shown in SEQ ID NO: 18. Concerning the nucleotide sequence, an amino acid sequence encoded by argS and an amino acid sequence encoded by lysA are shown in SEQ ID NOs: 19 and 20 respectively.

Example 5

Preparation of ddh from *Brevibacterium lactofermentum*

A ddh gene was obtained by amplifying the ddh gene from chromosomal DNA of *Brevibacterium lactofermentum* ATCC 13869 in accordance with the PCR method by using two oligonucleotide primers (SEQ ID NOs: 21, 22) prepared on the basis of a known nucleotide sequence of a ddh gene of *Corynebacterium glutamicum* (Ishino, S. et al., Nucleic Acids Res., 15, 3917 (1987)). An obtained amplified DNA fragment was digested with EcoT22I and AvaI, and cleaved edges were blunt-ended. After that, the fragment was inserted into a SmaI site of pMW119 to obtain a plasmid pDDH.

Next, pDDH was digested with SalI and EcoRI, followed by blunt end formation. After that, an obtained fragment was ligated with pUC18 having been digested with SmaI. A plasmid thus obtained was designated as pUC18DDH.

Figure 6:
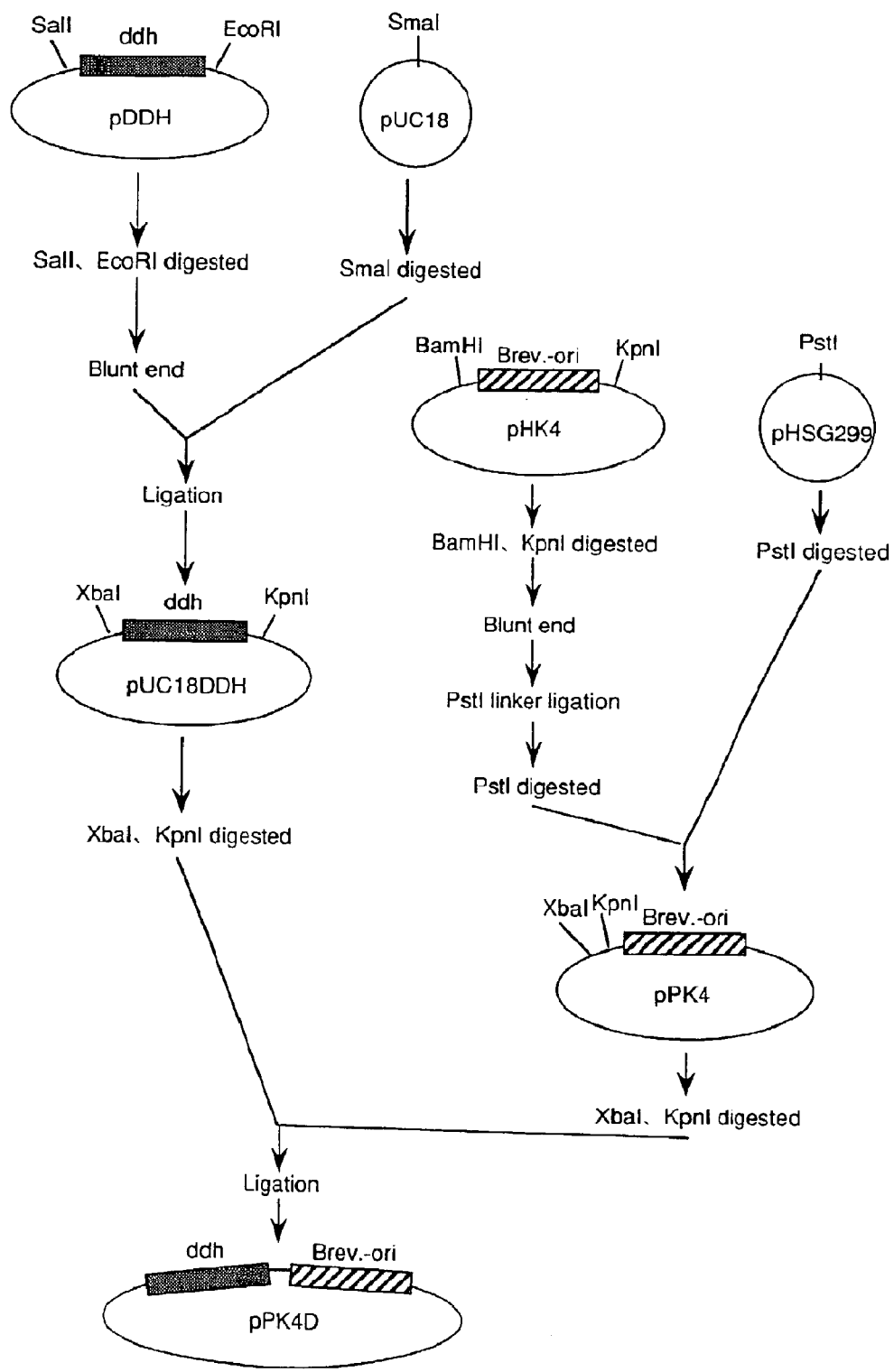
FIG. 6 illustrates a process of construction of a plasmid pPK4D comprising ddh and Brevi.-ori.

Brevi.-ori was introduced into pUC18DDH to construct a plasmid carrying ddh autonomously replicable in coryneform bacteria. pHK4 was digested with restriction enzymes KpnI and BamHI, and cleaved edges were blunt-ended. Blunt end formation was performed by using DNA Blunting kit (produced by Takara Shuzo) in accordance with a designated method. After the blunt end formation, a phosphorylated PstI linker (produced by Takara Shuzo) was ligated so that it was inserted into a PstI site of pHSG299. A plasmid constructed as described above was designated as pPK4. Next, pUC18DDH was digested with XbaI and KpnI, and a generated fragment was ligated with pPK4 having been digested with KpnI and XbaI. Thus a plasmid containing ddh autonomously replicable in coryneform bacteria was constructed. This plasmid was designated as pPK4D. The process of construction of pPK4D is shown in FIG. 6.

Example 6

Construction of Plasmid Comprising Combination of Mutant lysC and dapA

Figure 7:
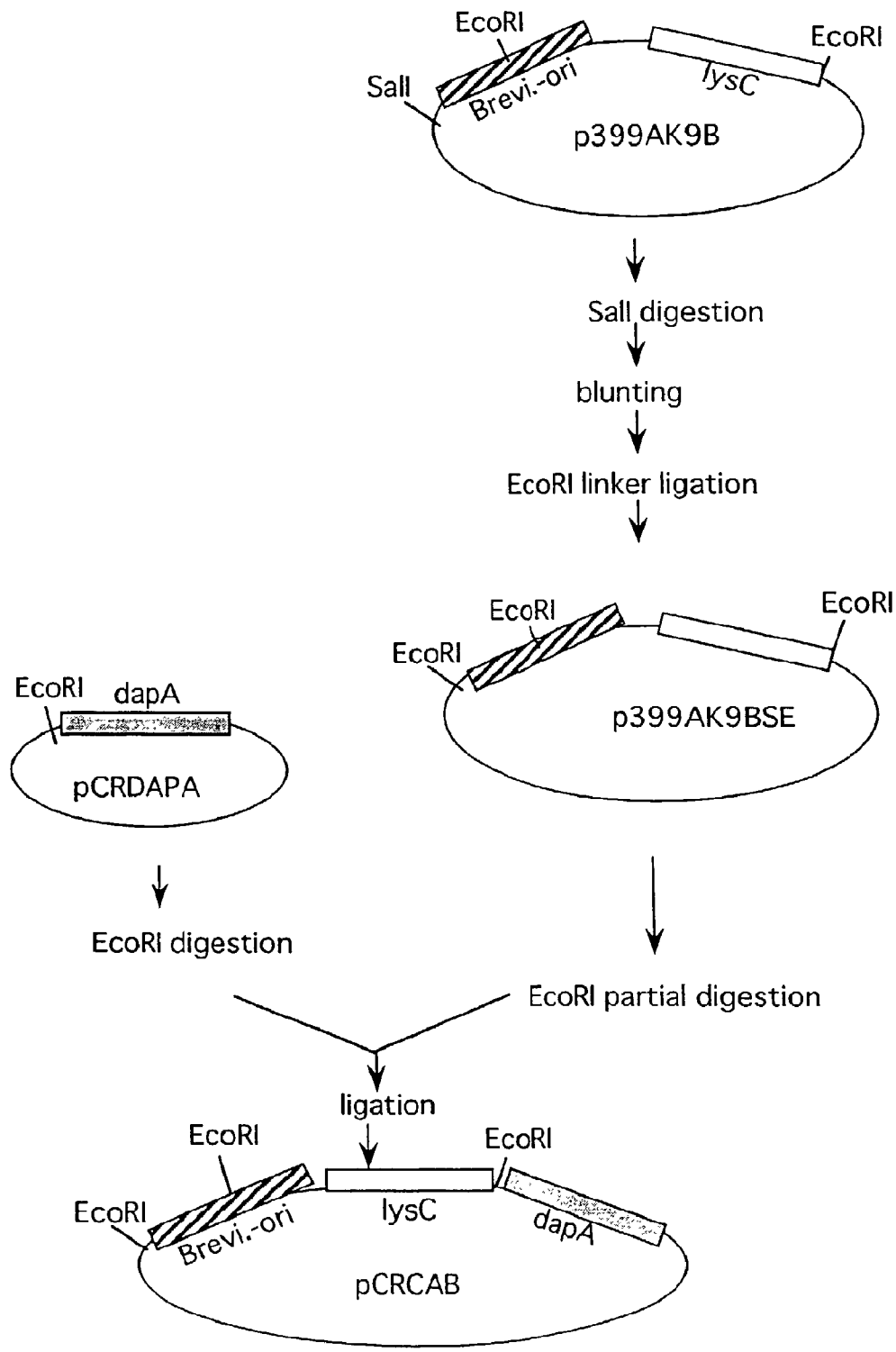
FIG. 7 illustrates a process of construction of a plasmid pCRCAB comprising lysC, dapB and Brevi.-ori.

A plasmid comprising mutant lysC, dapA, and replication origin of coryneform bacteria was constructed from the plasmid pCRDAPA comprising dapA and the plasmid p399AK9B comprising mutant lysC and Brevi.-ori. p399AK9B was completely degraded with SalI, and then it was blunt-ended, with which an EcoRI linker was ligated to construct a plasmid in which the SalI site was modified into an EcoRI site. The obtained plasmid was designated as p399AK9BSE. The mutant lysC and Brevi.-ori were excised as one fragment by partially degrading p399AK9BSE with EcoRI. This fragment was ligated with pCRDAPA having been digested with EcoRI. An obtained plasmid was designated as pCRCAB. This plasmid is autonomously replicable in *E. coli* and coryneform bacteria, and it gives kanamycin resistance to a host, the plasmid comprising a combination of mutant lysC and dapA. The process of construction of pCR-CAB is shown in FIG. 7.

Example 7

Construction of Plasmid Comprising Combination of Mutant lysC and dapB

A plasmid comprising mutant lysC and dapB was constructed from the plasmid p399AK9 having mutant lysC and the plasmid p399DPR having dapB. A fragment of 1,101 bp containing a structural gene of DDPR was extracted by digesting p399DPR with EcoRV and SphI. This fragment was ligated with p399AK9 having been digested with SalI and then blunt-ended and having been further digested with SphI to construct a plasmid comprising a combination of mutant lysC and dapB. This plasmid was designated as p399AKDDPR.

Figure 8:
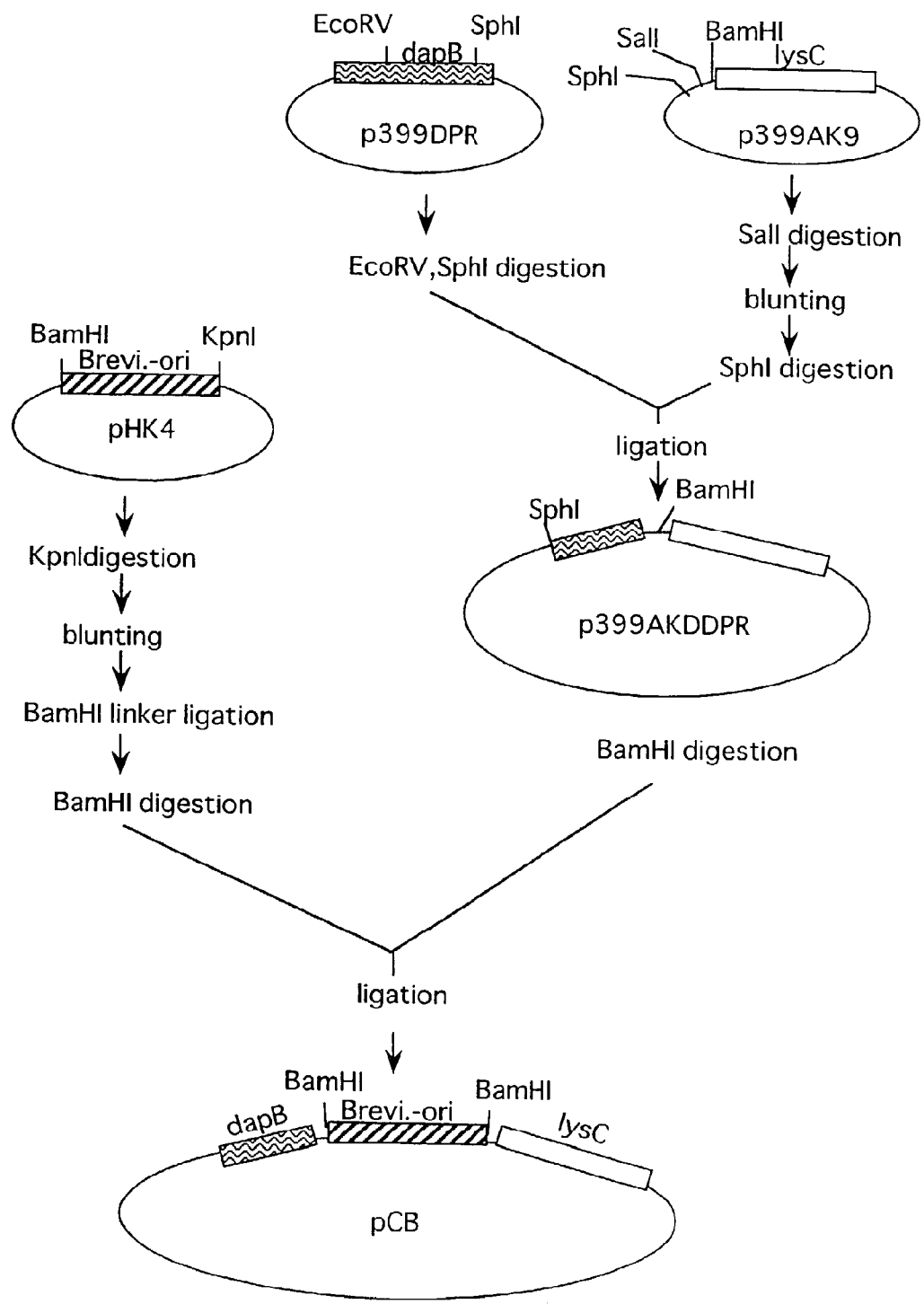
FIG. 8 illustrates a process of construction of a plasmid pCB comprising mutant lysC, dapB, and Brevi.-ori.

Next, Brevi.-ori was introduced into the obtained p399AKDDPR. The plasmid pHK4 containing Brevi.-ori was digested with a restriction enzyme KpnI (produced by Takara Shuzo), and cleaved edges were blunt-ended. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKDDPR having been also digested with BamHI to construct a plasmid containing mutant lysC and dapB autonomously replicable in coryneform bacteria. The constructed plasmid was designated as pCB. The process of construction of pCB is shown in FIG. 8.

Example 8

Construction of Plasmid Comprising Combination of dapA and dapB

The plasmid pCRDAPA comprising dapA was digested with KpnI and EcoRI to extract a DNA fragment containing dapA which was ligated with the vector plasmid pHSG399 having been digested with KpnI and EcoRI. An obtained plasmid was designated as p399DPS.

On the other hand, the plasmid pCRDAPB comprising dapB was digested with SacII and EcoRI to extract a DNA fragment of 2.0 kb containing a region coding for DDPR which was ligated with p399DPS having been digested with SacII and EcoRI to construct a plasmid comprising a combination of dapA and dapB. The obtained plasmid was designated as p399AB.

Figure 9:
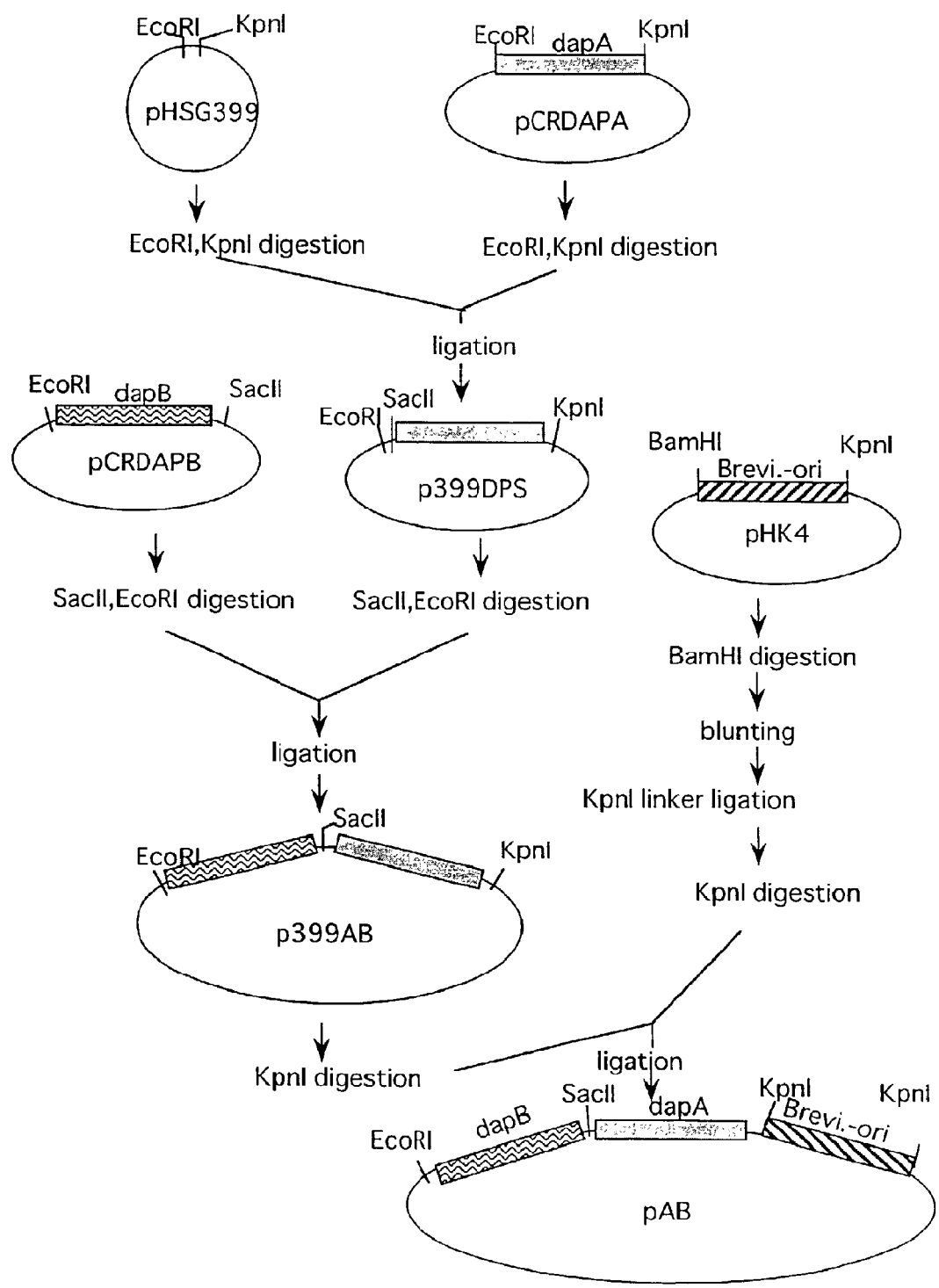
FIG. 9 illustrates a process of construction of a plasmid pAB comprising dapA, dapB and Brevi.-ori.

Next, Brevi.-ori was introduced into p399AB. pHK4 containing Brevi.-ori was digested with a restriction enzyme BamHI (produced by Takara Shuzo), and cleaved edges were blunt-ended. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p399AB having been also digested with KpnI to construct a plasmid containing dapA and dapB autonomously replicable in coryneform bacteria. The constructed plasmid was designated as pAB. The process of construction of pAB is shown in FIG. 9.

Example 9

Construction of Plasmid Comprising Combination of ddh and lysA

Figure 10:
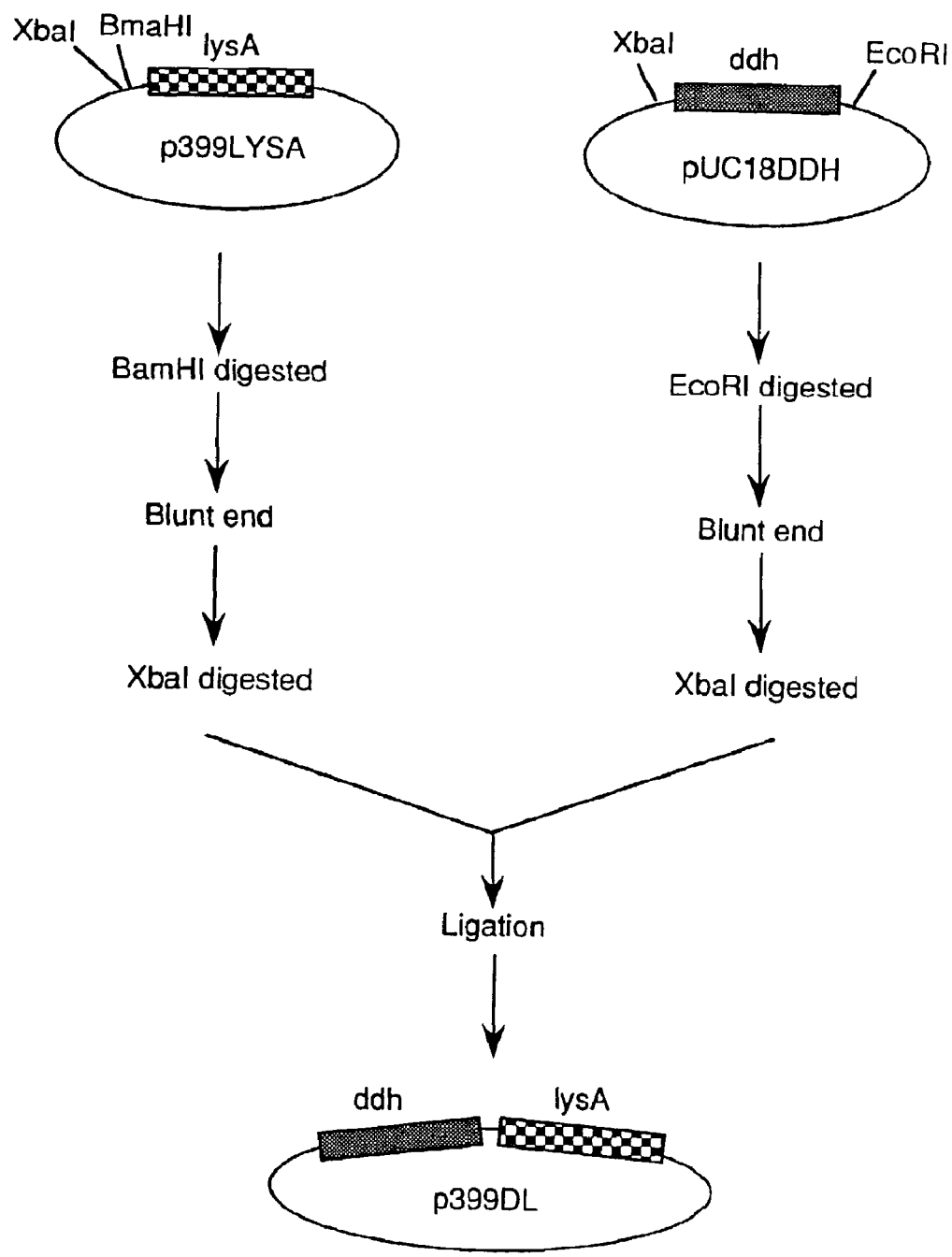
FIG. 10 illustrates a process of construction of a plasmid p399DL comprising ddh and lysA.

The plasmid pUC18DDH comprising ddh was digested with EcoRI and XbaI to extract a DNA fragment containing ddh. This ddh fragment was ligated with the plasmid p399LYSA comprising lysA having been digested with BamHI and XbaI with cleaved edges having been blunt-ended after the digestion. An obtained plasmid was designated as p399DL. The process of construction of p399DL is shown in FIG. 10.

Figure 11:
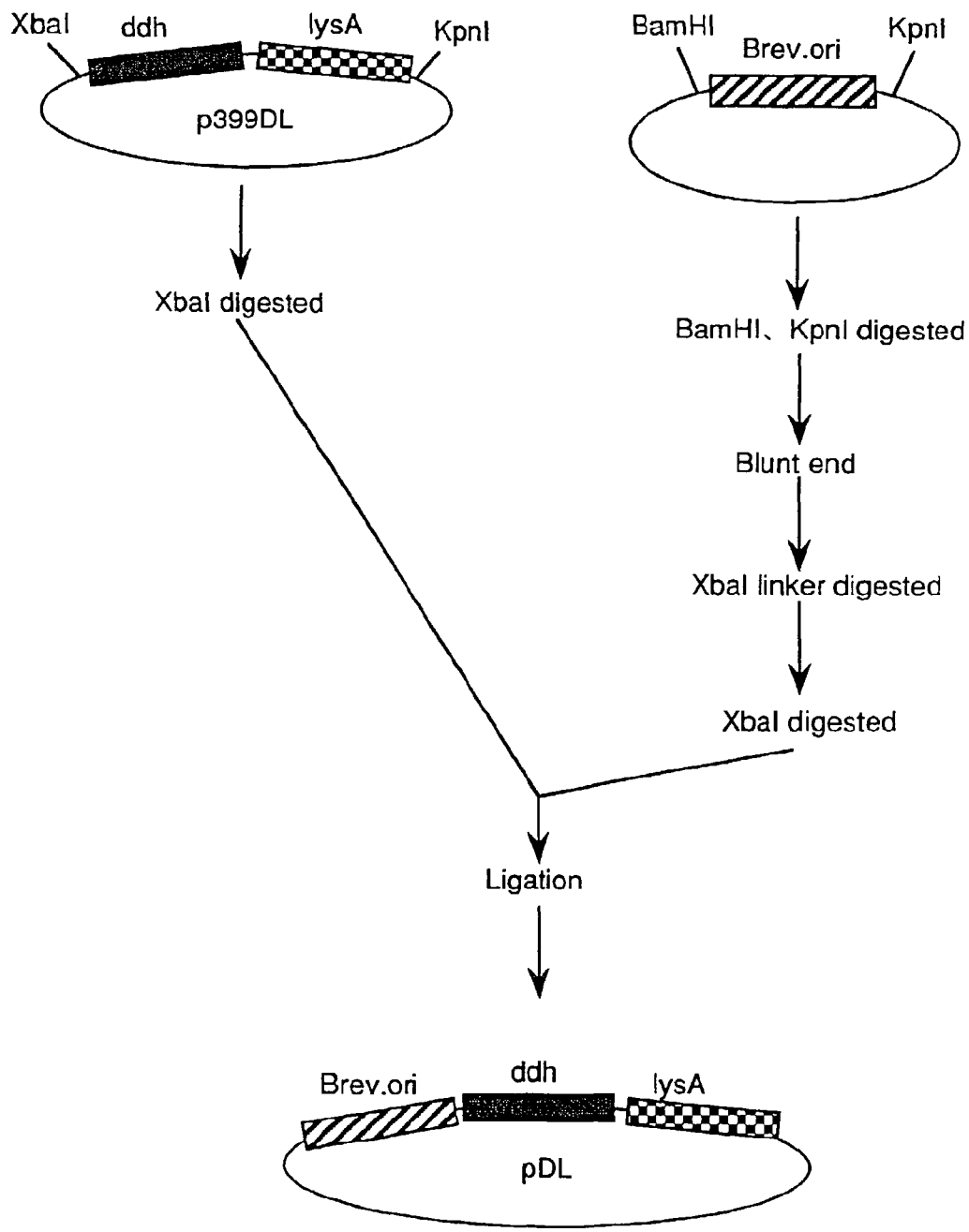
FIG. 11 illustrates a process of construction of a plasmid pDL comprising ddh, lysA and Brevi.-ori.

Next, Brevi.-ori was introduced into p399DL. pHK4 was digested with XbaI and BamHI, and cleaved edges were blunt-ended. After the blunt end formation, a phosphorylated XbaI linker was ligated to make modification so that the DNA fragment corresponding to the Brevi.-ori portion might be excised from pHK4 by digestion with only XbaI. This plasmid was digested with XbaI, and the generated Brevi.-ori DNA fragment was ligated with p399DL having been also digested with XbaI to construct a plasmid containing ddh and lysA autonomously replicable in coryneform bacteria. The constructed plasmid was designated as pDL. The process of construction of pDL is shown in FIG. 11.

Example 10

Construction of Plasmid Comprising Combination of Mutant lysC, dapA, and dapB p399DPS was degraded with EcoRI and SphI to form blunt ends followed by extraction of a dapA gene fragment. This fragment was ligated with the p399AK9 having been digested with SalI and blunt-ended to construct a plasmid p399CA in which mutant lysC and dapA co-existed.

The plasmid pCRDAPB comprising dapB was digested with EcoRI and blunt-ended, followed by digestion with SacI to extract a DNA fragment of 2.0 kb comprising dapB. The plasmid p399CA comprising dapA and mutant lysC was digested with SpeI and blunt-ended, which was thereafter digested with SacI and ligated with the extracted dapB fragment to obtain a plasmid comprising mutant lysC, dapA, and dapB. This plasmid was designated as p399CAB.

Figure 12:
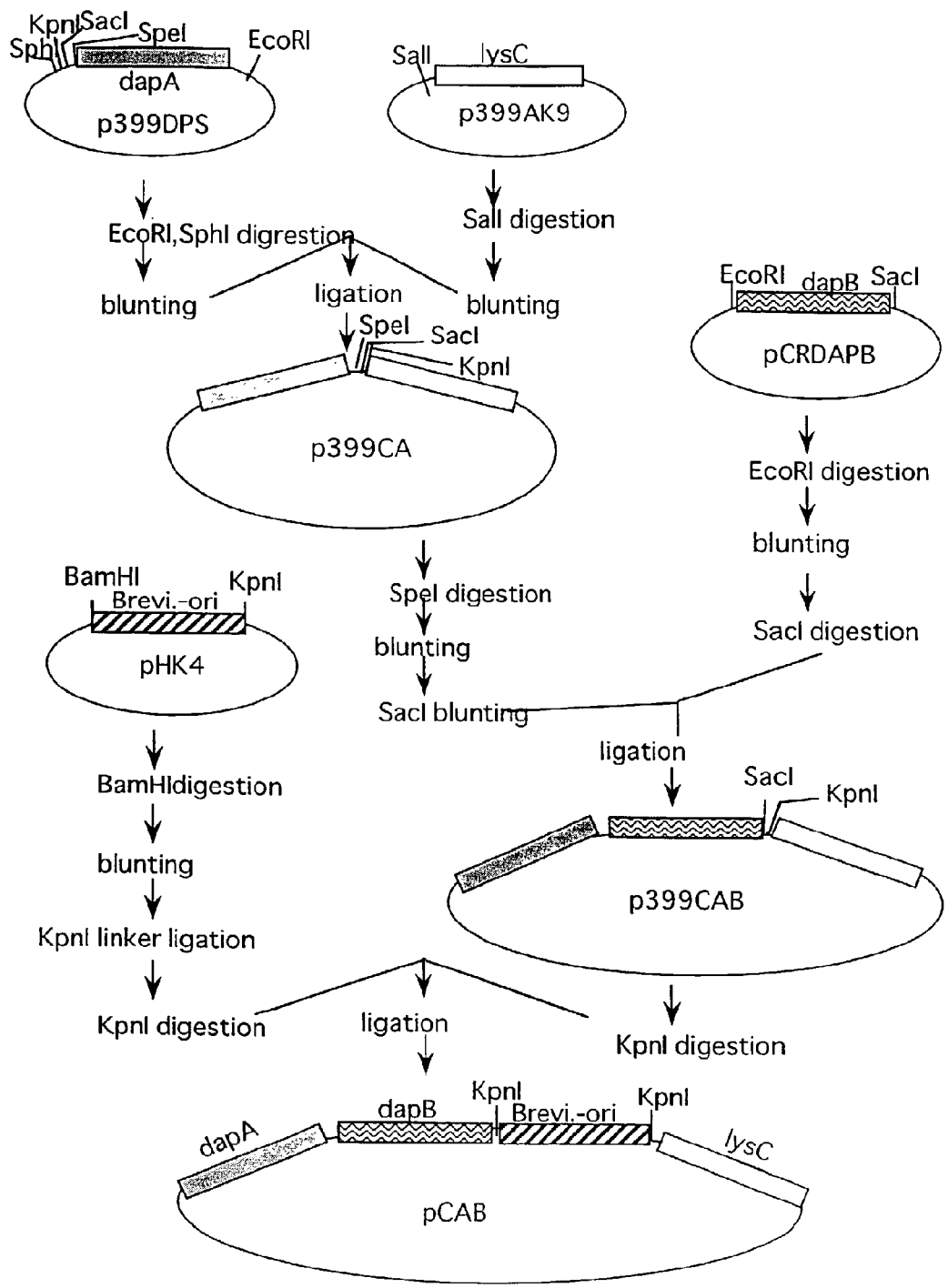
FIG. 12 illustrates a process of construction of a plasmid pCAB comprising mutant lysC, dapA, dapB, and Brevi.-ori.

Next, Brevi.-ori was introduced into p399CAB. The plasmid pHK4 comprising Brevi.-ori was digested with a restriction enzyme BamHI (produced by Takara Shuzo), and cleaved edges were blunt-ended. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p399CAB having been also digested with KpnI to construct a plasmid comprising a combination of mutant lysC, dapA, and dapB autonomously replicable in coryneform bacteria. The constructed plasmid was designated as pCAB. The process of construction of pCAB is shown in FIG. 12.

Example 11

Figure 13:
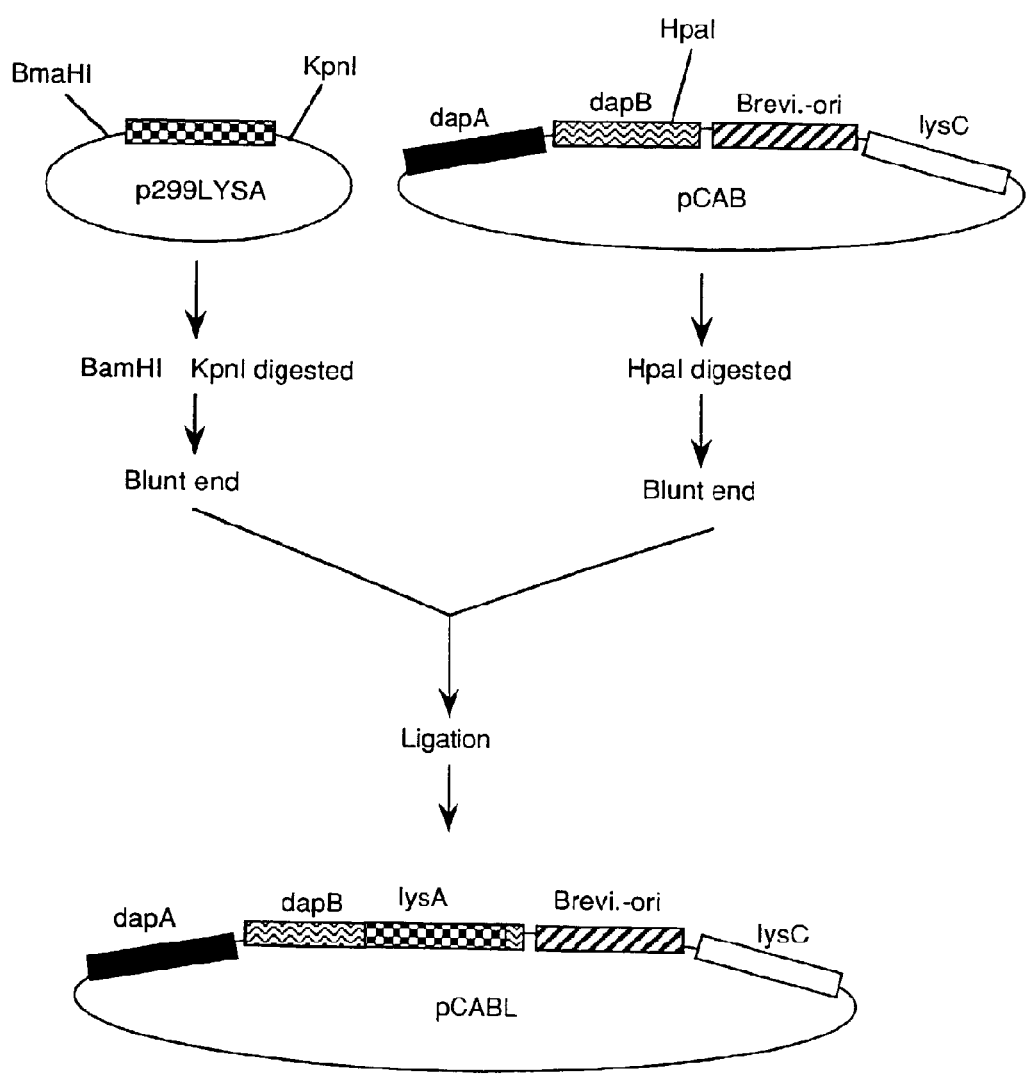
FIG. 13 illustrates a process of construction of a plasmid pCABL comprising mutant lysC, dapA, dapB, lysA, and Brevi.-ori.

Construction of Plasmid Comprising Combination of Mutant lysC, dapA, dapB, and lysA The plasmid p299LYSA comprising lysA was digested with KpnI and BamHI and blunt-ended, and then a lysA gene fragment was extracted. This fragment was ligated with pCAB having been digested with HpaI (produced by Takara Shuzo) and blunt-ended to construct a plasmid comprising a combination of mutant lysC, dapA, dapB, and lysA autonomously replicable in coryneform bacteria. The constructed plasmid was designated as pCABL. The process of construction of PCABL is shown in FIG. 13. It is noted that the lysA gene fragment is inserted into a HpaI site in a DNA fragment containing the dapB gene in pCABL, however, the HpaI site is located upstream from a promoter for the dapB gene (nucleotide numbers 611 to 616 in SEQ ID NO: 10), and the dapB gene is not decoupled.

Example 12

Figure 14:
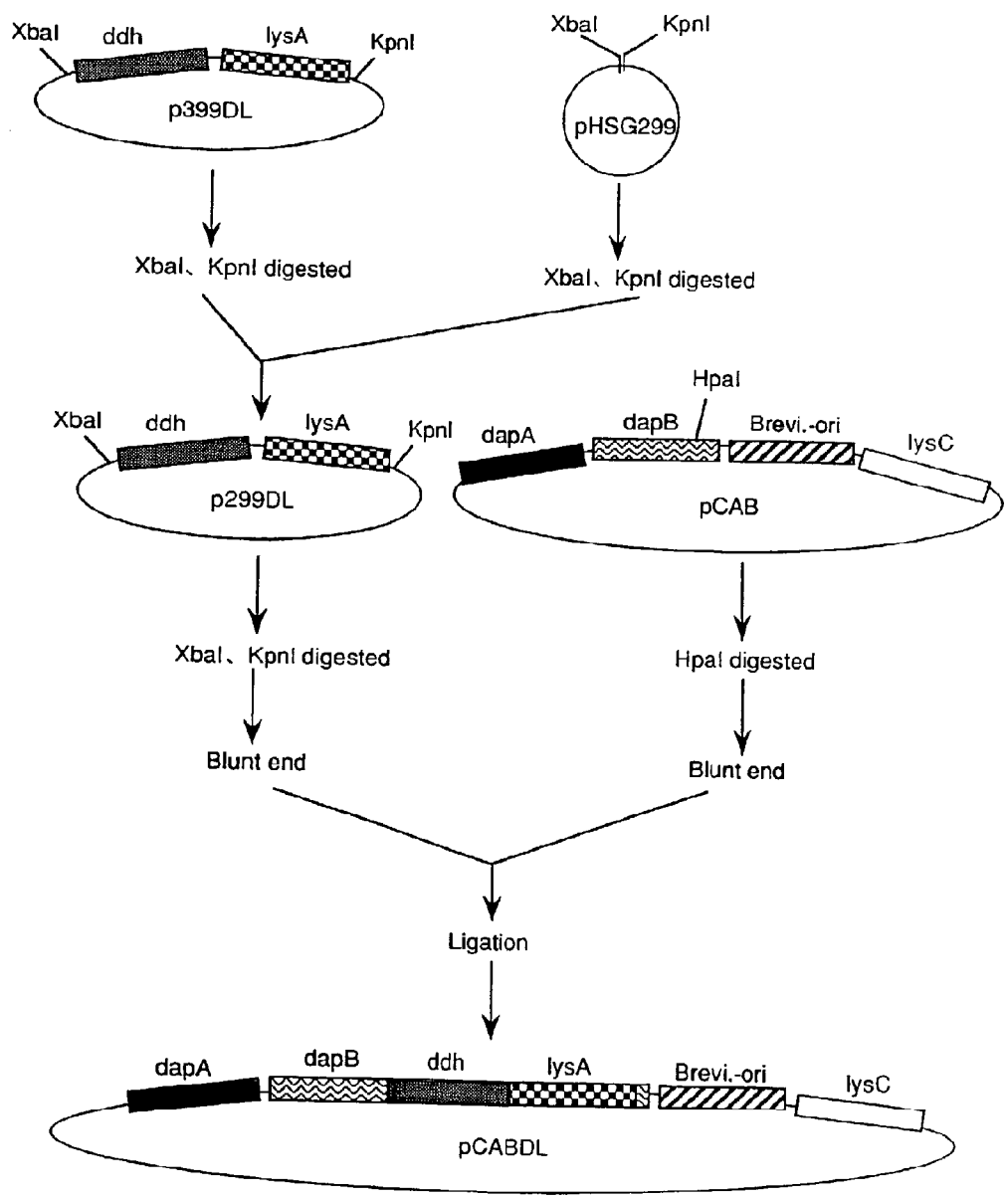
FIG. 14 illustrates a process of construction of a plasmid pCABDL comprising mutant lysC, dapA, dapB, ddh, lysA, and Brevi.-ori.

Construction of Plasmid Comprising Combination of Mutant lysC, dapA, dapB, ddh, and lysA pHSG299 was digested with XbaI and KpnI, which was ligated with p399DL comprising ddh and lysA having been digested with XbaI and KpnI. A constructed plasmid was designated as p299DL. p299DL was digested with XbaI and KpnI and blunt-ended. After the blunt end formation, a DNA fragment comprising ddh and lysA was extracted. This DNA fragment was ligated with the plasmid pCAB comprising the combination of mutant lysC, dapA, and dapB having been digested with HpaI and blunt-ended to construct a plasmid comprising a combination of mutant lysC, dapA, dapB, lysA and ddh autonomously replicable in coryneform bacteria. The constructed plasmid was designated as pCABDL. The process of construction of pCABDL is shown in FIG. 14.

Example 13

Introduction of Plasmids Comprising Genes for L-Lysine Biosynthesis into L-Lysine-Producing Bacterium of *Brevibacterium lactofermentum*

The plasmids comprising the genes for L-lysine biosynthesis constructed as described above, namely p399AK9B(Cm.sup.r), pDPSB(Km.sup.r), pDPRB(Cm.sup.r), pLYSAB(Cm.sup.r), pPK4D(Cm.sup.r), pCRCAB(Km.sup.r), pAB (Cm.sup.r), pCB(Cm.sup.r), pDL(Cm.sup.r), pCAB (Cm.sup.r), pCABL(Cm.sup.r), and pCABDL(Cm.sup.r) were introduced into an L-lysine-producing bacterium AJ11082 (NRRL B-11470) of *Brevibacterium lactofermentum* respectively. AJ11082 strain has a property of AEC resistance. The plasmids were introduced in accordance with an electric pulse method (Sugimoto et al., Japanese Patent Laid-open No. 2-207791). Transformants were selected based on drug resistance markers possessed by the respective plasmids. Transformants were selected on a complete medium containing 5 mu.g/ml of chloramphenicol when a plasmid comprising a chloramphenicol resistance gene was introduced, or transformants were selected on a complete medium containing 25 mu.g/ml of kanamycin when a plasmid comprising a kanamycin resistance gene was introduced.

Example 14

Production of L-Lysine

Each of the transformants obtained in Example 13 was cultivated in an L-lysine-producing medium to evaluate its L-lysine productivity. The L-lysine-producing medium had the following composition.

[L-Lysine-Producing Medium]

The following components other than calcium carbonate (per 1 L) were dissolved to make adjustment at pH 8.0 with KOH. The medium was sterilized at 115.degree. C. for 15 minutes, to which calcium carbonate (50 g) having been separately sterilized in hot air in a dry state was thereafter added.

1 Glucose 100 g (NH$_4$)$_2$SO$_4$ 55 g KH$_2$PO$_4$ 1 g MgSO$_4$.7H$_2$O 1 g Biotin 500 mu.g Thiamin 2000 mu.g FeSO$_4$.7H$_2$O 0.01 g MnSO$_4$.7H$_2$O 0.01 g Nicotinamide 5 mg Protein hydrolysate (Mamenou) 30 ml Calcium carbonate 50 g Each of the various types of the transformants and the parent strain was inoculated to the medium having the composition described above to perform cultivation at 31.5.degree. C. with reciprocating shaking. The amount of produced L-lysine after 40 or 72 hours of cultivation, and the growth after 72 hours (OD$_{562}$) are shown in Table 1. In the table, lysC* represents mutant lysC. The growth was quantitatively determined by measuring OD at 560 nm after 101-fold dilution.

TABLE 1

Accumulation of L-Lysine after Cultivation for 40 or 72 Hours

| Bacterial strain/plasmid | Introduced gene | Amount of produced L-lysine(g/L) 40 hrs | 72 hrs | Growth (OD$_{562}$/101) |
|---|---|---|---|---|
| AJ11082 | — | 22.0 | 29.8 | 0.450 |
| AJ11082/p399AK9B | lysC* | 16.8 | 34.5 | 0.398 |
| AJ11082/pDPSB | dapA | 18.7 | 33.8 | 0.410 |
| AJ11082/pDRB | dapB | 19.9 | 29.9 | 0.445 |
| AJ11082/pLYSAB | lysA | 19.8 | 32.5 | 0.356 |
| AJ11082/pPK4D | ddh | 19.0 | 33.4 | 0.330 |
| AJ11082/pCRCAB | lysC*, dapA | 19.7 | 36.5 | 0.360 |
| AJ11082/pAB | dapA, dapB | 19.0 | 34.8 | 0.390 |
| AJ11082/pCB | lysC*, dapB | 23.3 | 35.0 | 0.440 |
| AJ11082/pDL | ddh, lysA | 23.3 | 31.6 | 0.440 |
| AJ11082/pCAB | lysC*, dapA, dapB | 23.0 | 45.0 | 0.425 |
| AJ11082/pCABL | lysC*, dapA, dapB, lysA | 26.2 | 46.5 | 0.379 |
| AJ11082/pCABDL | lysC*, dapA, dapB, lysA, ddh | 26.5 | 47.0 | 0.409 |

As shown in Table 1, when mutant lysC, dapA, or dapB was enhanced singly, the amount of produced L-lysine was larger than or equivalent to that produced by the parent strain after 72 hours of cultivation, however, the amount of produced L-lysine was smaller than that produced by the parent strain after 40 hours of cultivation. Namely, the L-lysine-producing speed was lowered in cultivation for a short period. Similarly, when mutant lysC and dapA, or dapA and dapB were enhanced in combination, the amount of produced L-lysine was larger than that produced by the parent strain after 72 hours of cultivation, however, the amount of produced L-lysine was smaller than that produced by the parent strain after 40 hours of cultivation. Thus the L-lysine-producing speed was lowered.

On the other hand, when lysA or ddh was enhanced singly, or when lysA and ddh were enhanced in combination, the amount of produced L-lysine was larger than that produced by the parent strain after 40 hours of cultivation, however, the amount of produced L-lysine was consequently smaller than that produced by the parent strain after the long period of cultivation because of decrease in growth.

On the contrary, in the case of the strain in which dapB was enhanced together with mutant lysC, the growth was improved, the L-lysine-producing speed was successfully restored in the short period of cultivation, and the accumulated amount of L-lysine was also improved in the long period of cultivation. In the case of the strain in which three of mutant lysC, dapA, and dapB were simultaneously enhanced, the L-lysine productivity was further improved. Both of the L-lysine-producing speed and the amount of accumulated L-lysine were improved in a stepwise manner by successively enhancing lysA and ddh.

INDUSTRIAL APPLICABILITY

According to the present invention, the L-lysine-producing ability of coryneform bacteria can be improved, and the growth speed can be also improved.

The L-lysine-producing speed can be improved, and the productivity can be also improved in coryneform L-lysine-producing bacteria by enhancing dapB together with mutant lysC. The L-lysine-producing speed and the productivity can be further improved by successively enhancing dapA, lysA, and ddh in addition to the aforementioned genes.

---

What is claimed is:

1. A method for producing L-lysine comprising:
   (A) cultivating a coryneform bacterium in an appropriate medium, wherein said bacterium harbors:
      (1) aspartokinase prepared from a coryneform bacterium which is substantially densensitized to feedback inhibition by L-lysine and L-threonine,
      (2) a DNA sequence encoding dihydrodipicolinate reductase prepared from coryneform bacterium, wherein said DNA sequence expresses an enhanced amount of said dihydrodipicolinate reductase as compared to a wild-type coryneform bacterium, and
      (3) a DNA sequence encoding dihydrodipicolinate synthase, and
   (B) collecting L-lysine from the culture.

2. The method for producing L-lysine of claim 1, wherein said coryneform bacterium further comprises a DNA sequence encoding diaminopimelate decarboxylase.

3. The method for producing L-lysine of claim 2, wherein said coryneform bacterium further comprises a DNA sequence encoding diaminopimelate dehydrogenase.

4. The method for producing L-lysine of claim 1, wherein said dihydrodipicolinate synthase is selected from the group consisting of:
   (A) a protein comprising the amino acid sequence shown in SEQ ID NO. 15, and
   (B) a protein comprising an amino acid sequence which is substantially the same as SEQ ID NO. 15, and wherein said protein has the activity of dihydrodipicolinate synthase.

5. The method for producing L-lysine of claim 2, wherein said diaminopimelate decarboxylase is selected from the group consisting of:
   (A) a protein comprising the amino acid sequence shown in SEQ ID NO. 20, and
   (B) a protein comprising an amino acid sequence which is substantially the same as SEQ ID NO. 20, and wherein said protein has the activity of diaminopimelate decarboxylase.

6. The method for producing L-lysine of claim 3, wherein said diaminopimelate dehydrogenase is selected from the group consisting of:
   (A) a protein comprising the amino acid sequence shown in SEQ ID NO. 24, and
   (B) a protein comprising an amino acid sequence which is substantially the same as SEQ ID NO. 24, and wherein said protein has the activity of diaminopimelate dehydrogenase.

7. A method for producing L-lysine comprising:
   (A) cultivating a coryneform bacterium in an appropriate medium, wherein said bacterium comprises:
      (1) a mutant aspartokinase derived from coryneform bacterium, wherein said aspartokinase is substantially desensitized to feedback inhibition by L-lysine and L-threonine,
      (2) a DNA sequence encoding dihydrodipicolinate reductase which is selected from the group consisting of:
         (i) a protein comprising the amino acid sequence shown in SEQ ID NO. 11, and
         (ii) a protein comprising an amino acid sequence which is substantially the same as SEQ ID NO. 11, and wherein said protein has dihydrodipicolinate reductase activity,
      and wherein said DNA sequence is derived from a coryneform bacterium and is capable of expressing enhanced amounts of said dihydrodipicolinate reductase as compared to a wild-type coryneform bacterium, and
      (3) a DNA sequence encoding dihydrodipicolinate synthase, and
   (B) collecting L-lysine from the culture.

8. The method for producing L-lysine of claim 7, wherein said coryneform bacterium further comprises a DNA sequence encoding diaminopimelate decarboxylase.

9. The method for producing L-lysine of claim 8, wherein said coryneform bacterium further comprises a DNA sequence encoding diaminopimelate dehydrogenase.

10. The method for producing L-lysine of claim 7, wherein said dihydrodipicolinate synthase is selected from the group consisting of:
    (A) a protein comprising the amino acid sequence shown in SEQ ID NO. 15, and
    (B) a protein comprising an amino acid sequence which is substantially the same as SEQ ID NO. 15, and wherein said protein has the activity of dihydrodipicolinate synthase.

11. The method for producing L-lysine of claim 8, wherein said diaminopimelate decarboxylase is selected from the group consisting of:
    (A) a protein comprising the amino acid sequence shown in SEQ ID NO. 20, and
    (B) a protein comprising an amino acid sequence which is substantially the same as SEQ ID NO. 20, and wherein said protein has the activity of diaminopimelate decarboxylase.

12. The method for producing L-lysine of claim 9, wherein said diaminopimelate dehydrogenase is selected from the group consisting of:
    (A) a protein comprising the amino acid sequence shown in SEQ ID NO. 24, and
    (B) a protein comprising an amino acid sequence which is substantially the same as SEQ ID NO. 24, and wherein said protein has the activity of diaminopimelate dehydrogenase.

* * * * *